US012605076B1

(12) United States Patent
Bland

(10) Patent No.: US 12,605,076 B1
(45) Date of Patent: Apr. 21, 2026

(54) NON-INVASIVE BLOOD VISCOSITY MONITOR AND METHODS OF USE

(71) Applicant: Laura M. Bland, Edina, MN (US)

(72) Inventor: Laura M. Bland, Edina, MN (US)

( * ) Notice: Subject to any disclaimer, the term of this patent is extended or adjusted under 35 U.S.C. 154(b) by 210 days.

(21) Appl. No.: 17/445,574

(22) Filed: Aug. 20, 2021

Related U.S. Application Data

(60) Provisional application No. 63/068,157, filed on Aug. 20, 2020.

(51) Int. Cl.
| | |
|---|---|
| *A61B 5/02* | (2006.01) |
| *A61B 5/0265* | (2006.01) |
| *A61B 8/00* | (2006.01) |
| *A61B 8/06* | (2006.01) |

(52) U.S. Cl.
CPC ........ *A61B 5/02035* (2013.01); *A61B 5/0265* (2013.01); *A61B 8/06* (2013.01); *A61B 8/4416* (2013.01); *A61B 8/5223* (2013.01); *A61B 8/4227* (2013.01); *A61B 2562/0223* (2013.01); *A61B 2562/0285* (2013.01)

(58) Field of Classification Search
None
See application file for complete search history.

(56) References Cited

U.S. PATENT DOCUMENTS

| | | | |
|---|---|---|---|
| 8,180,427 B2 | 5/2012 | Phua et al. | |
| 2009/0203988 A1* | 8/2009 | Phua ........................ | G01F 1/56 |
| | | | 600/409 |

| | | | |
|---|---|---|---|
| 2013/0116519 A1* | 5/2013 | Wood ................... | A61B 5/0059 |
| | | | 600/322 |
| 2014/0316305 A1* | 10/2014 | Venkatraman ..... | A61B 5/02438 |
| | | | 600/595 |
| 2018/0085057 A1* | 3/2018 | Lynde ................... | A61B 5/681 |

(Continued)

FOREIGN PATENT DOCUMENTS

| | | | |
|---|---|---|---|
| EP | 3505094 A1 | | 7/2019 |
| JP | 2011234884 A | * | 11/2011 |

OTHER PUBLICATIONS

Eguchi et al. ("Non-contact optical hand-held viscosity sensor with incident angle and irradiation timing controls", vol. 26, No. 26 , Optics Express, 2018) (Year: 2018).*

(Continued)

*Primary Examiner* — Michael J Carey
*Assistant Examiner* — Marjan Saboktakin
(74) *Attorney, Agent, or Firm* — CM Law LLP; Michael P. Dunnam

(57) ABSTRACT

A wearable non-invasive blood viscosity monitor and methods of using the same are described. The blood viscosity monitor includes first and second sensors configured to sense blood parameters non-invasively from a subject and a processor circuit configured to generate an indication of blood viscosity using the sensed blood parameters from at least one of the first and second sensors and to generate a medical diagnostic using the indication of blood viscosity. An output circuit presents the medical diagnostic to alert a clinician about an elevated viscosity. The first and second sensors may be on the same or different fixation devices and adapted to provide measurements that are mixed and matched by the processor circuit to provide validation of measurements, averaging of measurements, or to select the most reliable data for each modality and measurement context.

30 Claims, 7 Drawing Sheets

(56)                    References Cited

U.S. PATENT DOCUMENTS

| | | | | |
|---|---|---|---|---|
| 2019/0101746 A1* | 4/2019 | Katsuyama | .......... | G02B 26/085 |
| 2020/0037898 A1* | 2/2020 | Dalan | ................ | A61B 5/02233 |
| 2021/0386299 A1* | 12/2021 | Hocking | .............. | A61B 5/4839 |
| 2022/0022758 A1* | 1/2022 | Eggers | ................... | A61B 8/488 |

OTHER PUBLICATIONS

Rostami et al. ("Fabrication of optical magnetic mirrors using bent and mushroom-like carbon nanotubes", Carbon, 48 (2010) 3659-3666) hereinafter "Rostami" (Year: 2010).*

Akl, Tony J. et al., "Quantifying tissue mechanical properties using photoplethysmography," Biomed Optics Express, vol. 5, Issue 7, Jul. 1, 2014, pp. 2362-2375.

antenna-theory.com, "Wearable Antennas," https://www.antenna-theory.com/antennas/wearable-antennas.php, lastaccessed Nov. 7, 2021, 5 pages.

Askarian, Behnam et al., "Monitoring of Heart Rate from Photoplethysmographic Signals Using a Samsung GalaxyNote8 in Underwater Environments" Sensors, vol. 19, Issue 13, Article 2846, Jun. 2019, 16 pages.

Beraia, M. et al., "Electromagnetic properties of the arterial blood flow," Biology, Engineering and Medicine, vol. 3, Issue 2, 2018, 8 pages.

Biopac Systems, Inc., "BIOPAC Blood Flow Monitor: Technique—Laser Doppler Flowmetry (LDF)," https://www.biopac.com/wp-content/uploads/LDF-laser-doppler-flowmetry.pdf Last accessed Nov. 26, 2021, 24 pages.

Bond, Charlotte et al., "Interferometer techniques for gravitational-wave detection," Living Reviews in Relativity, vol. 19, Article No. 3, Feb. 2017, 217 pages.

Ding, Ting-Jou et al., "Optical design of dual-elliptical mirrors of near-infrared absorption spectroscopy for diabetes detection," Optical Engineering, vol. 60, Issue 9, Article 091504, May 4, 2021, 9 pages.

Elgendi, Mohamed et al., "The use of photoplethysmography for assessing hypertension," npj Digital Medicine, vol. 2, Article 60, Jun. 26, 2019, 11 pages.

Esfandyarpour, Majid et al., "Optical emission near a high-impedance mirror," Nature Communications, vol. 9, Article 3224, Aug. 13, 2018, 24 pages.

Fu, Chenguang et al., "Thermoelectric signatures of the electron-phonon fluid in PtSn4," Materials Science, Feb. 26, 2018, 27 pages.

Hasan, Md Rabiul et al., "Dielectric optical nanoantennas," Nanotechnology, vol. 32, No. 20, IOP Publishing Ltd., Feb. 2021, 23 pages.

Holmes, Niall et al., "Balanced, bi-planar magnetic field and field gradient coils for field compensation in wearablemagnetoencephalography," Scientific Reports, vol. 9, Article No. 14196, Oct. 2, 2019, 30 pages.

Hu, Chengguo et al., "Carbon Nanotube-Based Electrochemical Sensors: Principles and Applications in BiomedicalSystems," Journal of Sensors, Nanomaterials for Chemical Sensing Technologies, vol. 2009, Article ID 187615, Jul. 9, 2009, 41 pages.

Humphries, Jr., Stanley, "Electric and Magnetic Field Lenses," Principles of Charged Particle Acceleration, FieldPrecision LLC, 1986, p. 108-136.

Jackson, Roland, "John Tyndall and the Early History of Diamagnetism," Annals of Science, vol. 72, Issue 4, Oct. 2, 2015, pp. 435-489.

Joseph, Jayaraj et al., "Magnetic sensor for non-invasive detection of blood pulse and estimation of arterial compliance," 2010 IEEE EMBS Conference on Biomedical Engineering and Sciences (IECBES), Nov. 30-Dec. 2, 2010, Kuala Lumpur, Malaysia, pp. 170-175.

Kamišali'C, Aida et al., "Sensors and Functionalities of Non-Invasive Wrist-Wearable Devices: A Review," Sensors, May 25, 2018, vol. 18, Issue 6, Article 1714, 33 pages.

Karvelas, Evangelos et al., "Effect of Micropolar Fluid Properties on the Blood Flow in a Human Carotid Model,"Fluids, vol. 5, Issue 3, Jul. 29, 2020, 16 pages.

Kimura, Wayne D., "What are electromagnetic waves?" Electromagnetic Waves and Lasers, Nov. 2017, 33 pages.

Kimura, Tsunehisa et al., "Faraday Diamagnetism under Slowly Oscillating Magnetic Fields," Journal of Magnetism and Magnetic Materials, vol. 451, 2017, pp. 65-69 (Abstract only).

Klingeler, Rüdiger et al., "Carbon nanotube based biomedical agents for heating, temperature sensoring and drug delivery," International Journal of Hyperthermia, vol. 24, Issue No. 6, Sep. 2008, pp. 496-505.

La Mura, Monica et al., "Equivalent Electrical Circuit Modeling of CNT-Based Transparent Electrodes," AppliedSciences, vol. 11, Issue 8, Article 3408, Apr. 2021, 17 pages.

Lazazzera, Remo et al., "A New Wearable Device for Blood Pressure Estimation Using Photoplethysmogram,"Sensors, Switzerland, vol. 19, Issue 11, Jun. 2019, 29 pages.

Li, Kebin et al., "Nanoimprint Lithography and Its Application in Tissue Engineering and Biosensing," ComprehensiveBiotechnology, Dec. 2011, Elsevier B.V., pp. 125-139.

Liu, Sheng et al., "Optical Magnetic Mirrors without Metals," Optica, vol. 1, Issue 4, Oct. 20, 2014, pp. 250-256.

Liu, Shike et al., "Measurement of the refractive index of whole blood and its components for a continuous spectralregion," Journal of Biomedical Optics, vol. 24, No. 3, Mar. 2019, 6 pages.

Lumen Physics, "The Hall Effect," https://courses.lumenlearning.com/physics/chapter/22-6-the-hall-effect/ Last accessed Nov. 16, 2021, 6 pages.

Ma, A. W. K. et al., "A review of the microstructure and rheology of carbon nanotube suspensions," Proceedings of theInstitution of Mechanical Engineers, Part N: Journal ofNanomaterials, Nanoengineering and Nanosystems, vol. 222, Issue 3, Jun. 19, 2009, pp. 71-94.

Marques Lameirinhas, Richardo A. et al., "A Sensor Based on Nanoantennas," Applied Sciences, vol. 10,Issue 19, No. 6837, Sep. 2020, 23 pages.

Morris, Robert H, et al., "Magnetic resonance sensors," Sensors, vol. 14, Issue 11, Nov. 17, 2014, Basel, Switzerland, pp. 21722-21725.

Murzin, Dmitry et al., "Ultrasensitive Magnetic Field Sensors for Biomedical Applications," Sensors, vol. 20, Issue6, Article 1569, Mar. 11, 2020, 32 pages.

Naaman, Ron et al., "Chiral molecules and the electron spin," Nature Reviews Chemistry, vol. 3, Mar. 25, 2019, 11 pages.

Nesci, Antonello, "Measuring amplitude and phase in optical fields with subwavelength structures," Université deNeuchâtelInstitut de Microtechnique, Nov. 2001, 104 pages.

Ni, Chi-Nung, "Electronic, Optical, and Mechanical Characterization of Zero- and One-Dimensional Nanostructures,"University of San Diego, California, 2008, 145 pages.

Ohio Supercomputer Center, "Magnetism can control heat, sound." ScienceDaily, May 28, 2015, www.sciencedaily.com/releases/2015/05/150528153621.htm, last accessed Nov. 25, 2021, 2 pages.

Park, Sei Jin et al., "Modulation of the effective density and refractive index of carbon nanotube forests via nanoimprint lithography," Carbon, vol. 129, Apr. 2018, version https://www.sciencedirect.com/science/article/pii/ S0008622317311934, last accessed Nov. 7, 2021, 20 pages.

Patel, Bishan et al., "Wearable Device Testing," WhaleTeq, May 12, 2021, 33 pages.

Phillips, Andy, "Magnetic Field Sensors: A Comparison of Two Technologies," Medical Design Briefs, Sep. 1, 2019, https://www.medicaldesignbriefs.com/component/content/article/mdb/features/technology-leaders/35094 Lastaccessed Nov. 26, 2021, 5 pages.

Phua, Chee Teck et al., "Non-invasive measurement of blood flow using magnetic disturbance method," 2009International Conference on Biomedical and Pharmaceutical Engineering, Institute of Electrical and ElectronicsEngineers, Dec. 2-4, 2009, 4 pages.

Phua, Chee Teck, "Novel method of blood pulse and flow measurement using the disturbance created by blood flowing through a localized magnetic field," Systèmes de communication et Microsystèmes Electronique, UniversitéParis, Sep. 21, 2012, 214 pages.

(56) References Cited

OTHER PUBLICATIONS

Picardi, Michela F. et al., "Janus and Huygens' dipolar sources for near-field directionality" Physics Review Letters, vol. 120, 117402, Mar. 15, 2018, 9 pages.

Pop, G.A.M. et al., "On-Line Electrical Impedance Measurement for Monitoring Blood Viscosity during On-Pump HeartSurgery," European Surgical Research, vol. 35, Issue 5, Oct. 2004, pp. 259-265.

Reddy, Satish et al., "Measuring the surface properties of a Novel 3-D Artificial Magnetic Material," ProcediaMaterials Science, vol. 10, Dec. 2015, pp. 632-637.

Rostami, Habib et al., "Fabrication of optical magnetic mirrors using bent and mushroom-like carbon nanotubes,"Carbon, vol. 48, Issue 13, 2010, pp. 3659-3666.

Rowe, David J. et al., "Improved Split-Ring Resonator for Microfluidic Sensing," IEEE Transactions on MicrowaveTheory and Techniques, vol. 62, Issue 3, Mar. 2014, pp. 689-699.

Samadishadlou, Mehrdad et al., "Magnetic carbon nanotubes: preparation, physical properties, and applications in biomedicine," Artificial Cells, Nanomedicine, and Biotechnology, vol. 46, Issue 7, 2018, pp. 1314-1330.

Sanli, Abdulkadir et al., "Electrical impedance analysis of carbon nanotube/epoxy nanocompositebased piezoresistive strain sensors under uniaxial cyclic static tensile loading," Journal of Composite Materials, vol. 54,Issue 6, Mar. 2020, 11 pages.

Saqr, Khalid M. et al., "Physiologic blood flow is turbulent," Scientific Reports, vol. 10, Article 15492, Sep. 2020, 12 pages.

Science of Signatures, "SoS A Los Alamos National Laboratory Science Pillar," Los Alamos NationalLaboratory Science of Signatures Strategy, 2014, 28 pages.

Sciencedirect, "Photoelectric Plethysmography—An overview of ScienceDirect Topics," https://www.sciencedirect.com/topics/nursing-and-health-professions/photoelectric-plethysmography Last accessed Nov. 27, 2021, 11 pages.

Shine, Augustine et al., "Non invasive estimation of blood pressure using a linear regression model from the photoplethysmogram (PPG) signal," International Conference on Information Technology, Electronics and Communications, vol. 22, Bangalore, India, Mar. 30-31, 2013, pp. 31-35.

Shit, G. C. et al., "Pulsatile flow and heat transfer of blood in an overlapping vibrating atherosclerotic artery: A numerical study," Mathematics and Computers in Simulation (MATCOM), Elsevier, vol. 166, 2019, pp. 432-450.

Sinatra, Francy L., "Understanding the Interaction Between Blood Flow and an Applied Magnetic Field," Universityof South Florida, 2010, 81 pages.

Sun, Ge et al., "An Algorithm for the Noninvasive and Personalized Measurement of Microvascular Blood and Viscosity Using Physiological Parameters," BioMed Research International, vol. 2020, Article ID 7013212,Sep. 2020, 7 pages.

Svela, Andreas O. et al., "Coherent suppression of backscattering in optical microresonators," Light: Science &Applications, vol. 9, Article No. 204, Dec. 23, 2020, 8 pages.

Sviridova, Nina et al., "Human photoplethysmogram: new insight into chaotic characteristics," Chaos, Solitons &Fractals, vol. 77, Elservier, Ltd., Aug. 2015, pp. 53-63.

Tamura, Toshiyo et al., "Wearable Photoplethysmographic Sensors—Past and Present," Electronics, Apr. 23, 2014, vol. 3, Issue 2, pp. 282-302.

Thanner, Christine et al., "UV Nanoimprint Lithography: Geometrical Impact on Filling Properties of NanoscalePatterns," Nanomaterials, vol. 11, Issue 3, Article 822, Basel, Switzerland, Mar. 23, 2021, 13 pages.

U.S. Department of Transportation—Federal Aviation Administration, "Chapter 4.1.7—Returningfrom Space: Re-entry," pp. 309-339.

Urone, Paul Peter et al., Viscosity and Laminar Flow; Poiseuille's Law, OpenStax CNX, Jul. 11, 2021, https://phys. libretexts.org/@go/page/1574.

van de Vosse, F.N. et al., Cardiovascular Fluid Mechanics, Technische Universiteit Eindhoven, 1998, 130 pages.

Van Tiggelen, Bart A. e al., "Manipulating Light with a Magnetic Field," Optical Properties of Nanostructured Random Media: Topics in Applied Physics, vol. 82, Jan. 2002, Springer, Berlin, Heidelberg, pp. 275-302.

Wei, Lei et al., "The Recent Progress of MEMS/NEMS Resonators," Micromachines 2021, vol. 12, Issue 6, Article724; Jun. 19, 2021, 29 pages.

Weidman, Joseph et al., "Effect of electrolyzed high-pH alkaline water on blood viscosity in healthy adults," Journal of the International Society of Sports Nutrition, vol. 13, Article 45, Nov. 28, 2016, 13 pages.

Wikipedia, "Carbon nanotube," https://en.wikipedia.org/wiki/Carbon_nanotube Last accessed Nov. 27, 2021, 25pages.

Wikipedia, "Faraday effect," https://en.wikipedia.org/wiki/Faraday_effect, last accessed Nov. 7, 2021.

Wikipedia, "Hall Effect." https://en.wikipedia.org/wiki/Hall_effect Last accessed Nov. 26, 2021, 10 pages.

Wikipedia, "Hemorheology," https://en.wikipedia.org/wiki/Hemorheology Last accessed Nov. 26, 2021, 9 pages.

Wikipedia, "Maxwell's equations," https://en.wikipedia.org/wiki/Maxwell%27s_equations Last accessed Nov. 27, 2021, 17 pages.

Wikipedia, "Refractive index," https://en.wikipedia.org/wiki/Carbon_nanotube Last accessed Nov. 27, 2021, 16 pages.

Xu, Tieying et al., "Characterization of red blood cell microcirculatory parameters using a bioimpedance microfluidicdevice," Scientific Reports, vol. 10, Article No. 9869, Jun. 17, 2020.

Yanase, Kazutaka et al., "Boundary layer control by a fish: Unsteady laminar boundary layers of rainbow troutswimming in turbulent flows." Biology open, vol. 5, Issue 12, Dec. 15, 2016, pp. 1853-1863.

Yang, Siming et al., "From Flexible and Stretchable Meta-Atom to Metamaterial: A Wearable Microwave Meta-Skinwith Tunable Frequency Selective and Cloaking Effects," Scientific Reports, vol. 6, Article No. 21921, Feb. 2016, 8 pages.

Zhang, Qingxue et al., "Highly wearable cuff-less blood pressure and heart rate monitoring with single-arm electrocardiogram and photoplethysmogram signals," BioMedical Engineering OnLine vol. 16, Article No. 23,Feb. 16, 2017, 20 pages.

Zhang, Wuxu et al., "The application of carbon nanotubes in target drug delivery systems for cancer therapies,"Nanoscale Research Letters, vol. 6, Article 555, Oct. 13, 2011, 22 pages.

Zhang, Yang et al., "Mechanism of Magnetic Pulse Wave Signal for Blood Pressure Measurement," Journal ofBiomedical Science and Engineering, vol. 9, Issue 10B, Sep. 2016, pp. 29-36.

Zhao, J. M. et al., "Electromagnetic energy storage and power dissipation in nanostructures," Journal of Quantitative Spectroscopy and Radiative Transfer, vol. 151, Jan. 2015, 38 pages.

\* cited by examiner

NON-INVASIVE BLOOD VISCOSITY MONITOR AND METHODS OF USE

PRIORITY CLAIM

This application claims priority to U.S. Provisional Patent Application No. 63/068,157 entitled "Non-Invasive Blood Viscosity Monitor and Methods of Use" filed Aug. 20, 2020. The content of that patent application is hereby incorporated by reference in its entirety.

TECHNICAL FIELD

This document relates generally to medical devices, and more particularly, to devices and methods of non-invasive measurement of blood viscosity.

BACKGROUND

Blood viscosity is a measure of the resistance of blood to flow and is a critical determinant of friction against the vessel walls, the rate of venous return, the work required for the heart to pump blood, and the amount of oxygen transported to tissues and organs. These functions of the cardiovascular system are directly related to vascular resistance, preload, afterload, and perfusion. The primary determinants of blood viscosity are hematocrit, red blood cell deformability, red blood cell aggregation, and plasma viscosity, which is determined by its macromolecular components and water-content.

High blood viscosity, or hyperviscous blood, can be harmful in many ways. It increases cardiac demand and inhibits oxygen delivery to tissue. It may also cause damage to the blood vessel wall lining. Highly viscous blood forms turbulent flow at a bifurcation point of a segment of a blood vessel, damaging the lateral walls, and initiating an atherosclerotic process that facilitates plaque formation.

High blood viscosity can have acute and chronic consequences. Chronic high blood viscosity may exacerbate a number of disease states. A sudden increase in blood viscosity may lead to cardiovascular events such as heart attack, or cerebrovascular events such as stroke. Coronary artery disease and stroke are leading causes of deaths attributable to cardiovascular disease and have been major sources of medical costs.

High blood viscosity can be associated with high plasma viscosity due to dehydration. As such, an abnormally high blood viscosity may be used as an indicator of hydration. Clinically, the dehydrated state (which is linked to elevated plasma viscosity) has been conventionally evaluated using parameters such as blood pressure, urine concentration, or hemoglobin/hematocrit levels. Fluid loss is replaced if the subject is deemed dehydrated, or volume-down, by indicators such as these.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

The various elements shown in the figures are not drawn to scale unless otherwise indicated. The dimensions of the various elements may be enlarged or reduced in the interest of clarity. The several figures depict one or more implementations and are presented by way of example only and should not be construed as limiting. Included in the drawings are the following figures.

DETAILED DESCRIPTION

Figure 1A:
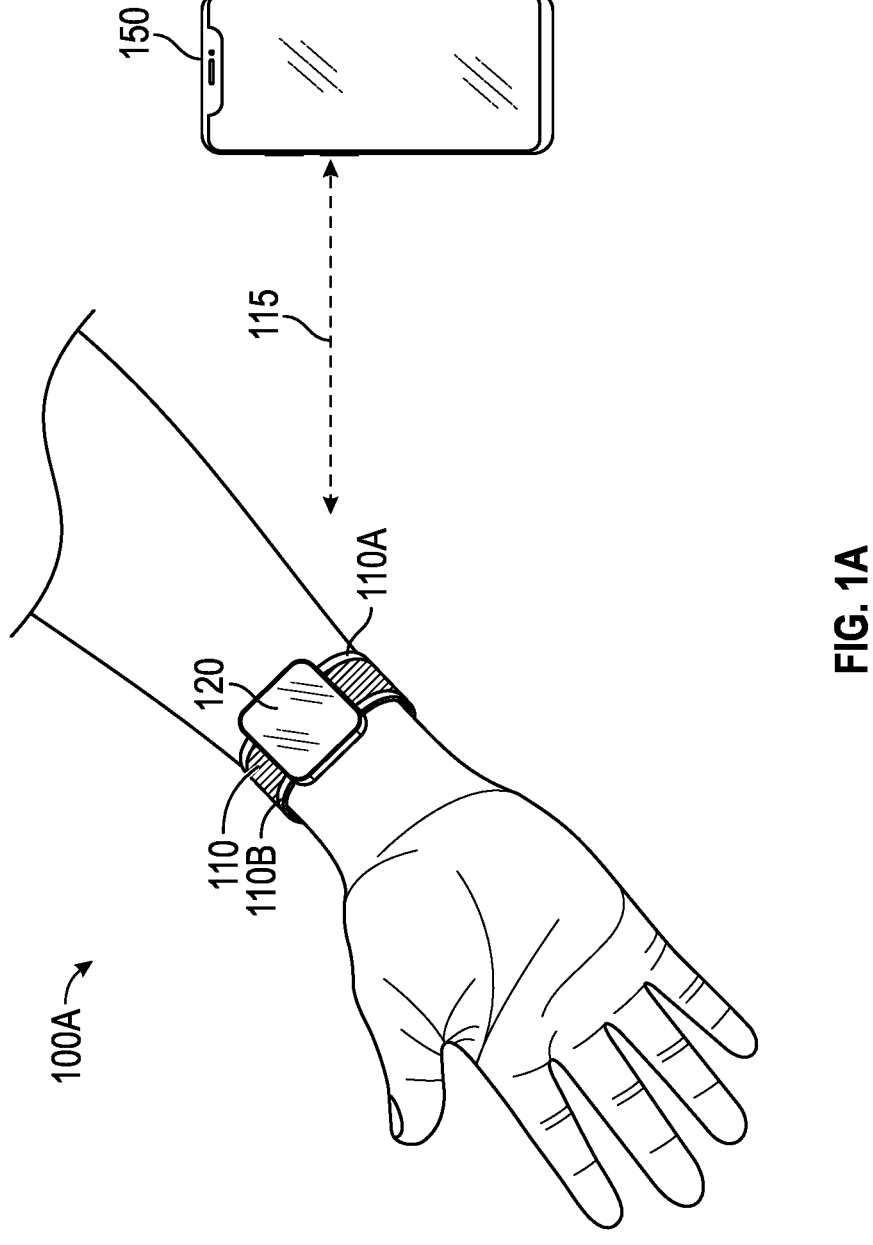
FIG. 1A illustrates a wrist-worn non-invasive blood viscosity monitor detachably affixed to a wrist.

In the assessment of viscosity, parameters such as blood pressure, urine concentration, or hemoglobin/hematocrit levels are indirect indicators of viscosity and have drawbacks. Blood viscosity or plasma viscosity are independent factors from the indirect indicators such as blood pressure or urine concentration, and typically do not follow the same time course of regulation as those indirect indicators. The present inventor has recognized that blood viscosity generally lags behind indirect indicators (e.g., blood pressure, urine concentration, or hemoglobin or hematocrit levels) associated with needed fluid resuscitation. As such, even when some of the indirect viscosity indications have returned to normal after fluid resuscitation, this is not a guarantee that blood viscosity has returned to its baseline homeostasis; instead, blood viscosity still may be elevated. Consequently, it may take even more fluid to overcome the delayed recovery of viscosity to bring the blood flow back to its normal level. This underscores the potential problem with many of the commercially available hydration-tracking bands and devices. They are not sufficient, because they also fail to address such differences in temporal responses to fluid replacement between blood viscosity and the indirect indicators as discussed above. For these reasons, the chronic dehydrated state may be grossly underappreciated. So, although the health-minded consumer wears a hydration-tracking band or device to be proactive, the risks and/or acceleration of cardiovascular and cerebrovascular disease may still be progressing.

The current gold standard of blood viscosity measurement involves a lab test of a blood sample using a viscometer or a rheometer. Such a test method is fraught with challenges. It does not adequately address non-Newtonian blood flow in the vascular system vessel. The non-Newtonian flow is characterized by varying viscosity under varying forces applied to the blood. Additionally, the blood sample is usually taken via venipuncture, an invasive approach that can be painful. Moreover, the time interval for results is too prolonged. There is no capability for real-time, or continuous viscosity reading. This is undesirable from a convenience and practicality standpoint, particularly for some patients in circumstances where ambulatory viscosity assessment is needed and/or demanded in an acute or continuous fashion. The expectation is that devices will allow for continuous monitoring and immediate feedback in any ambulatory setting in order to provide clinical and economic value. For at least the foregoing reasons, the present inventor has recognized an unmet need for an ambulatory blood viscosity monitor that can provide non-invasive, continuous blood viscosity assessment. Such a monitor may improve the technology of ambulatory physiological monitoring, and more effectively prevent cardiovascular or cerebrovascular events. As such, overall medical cost savings may be realized.

A non-invasive blood viscosity monitor is described herein that includes a device or system, that through assessment of various properties of the blood, yields the result of blood viscosity, but may not be limited to this result. The monitor as described in the present document, and the methods of using the same, may be used for medical diagnostics, patient screening, monitoring, continuous or otherwise, by a user and/or a clinician, or for therapeutic purposes.

An exemplary wearable non-invasive blood viscosity monitor includes first and second sensors configured to sense blood parameters non-invasively from a subject and a processor circuit configured to generate an indication of blood viscosity using the sensed blood parameters from at least one of the first and second sensors and to generate a medical diagnostic using the indication of blood viscosity. An output circuit presents the medical diagnostic to alert a clinician about an elevated viscosity. The first and second sensors may be on the same or different fixation devices and adapted to provide measurements that are mixed and matched by the processor circuit to provide validation of measurements, averaging of measurements, or to select the most reliable data for each modality and measurement context.

The following detailed description includes systems, methods, techniques, instruction sequences, and computer program products illustrative of examples set forth in the disclosure. Numerous details and examples are included for the purpose of providing a thorough understanding of the disclosed subject matter and its relevant teachings. Those skilled in the relevant art, however, may understand how to apply the relevant teachings without such details. Aspects of the disclosed subject matter are not limited to the specific devices, systems, and methods described because the relevant teachings can be applied or practiced in a variety of ways. The terminology and nomenclature used herein is for the purpose of describing particular aspects only and is not intended to be limiting. In general, well-known instruction instances, protocols, structures, and techniques are not necessarily shown in detail.

The term "connect," "connected," "couple," and "coupled" as used herein refers to any logical, optical, physical, or electrical connection, including a link or the like by which the electrical or magnetic signals produced or supplied by one system element are imparted to another coupled or connected system element. Unless described otherwise, coupled, or connected elements or devices are not necessarily directly connected to one another and may be separated by intermediate components, elements, or communication media, one or more of which may modify, manipulate, or carry the electrical signals. The term "on" means directly supported by an element or indirectly supported by the element through another element integrated into or supported by the element.

Additional objects, advantages and novel features of the examples will be set forth in part in the following description, and in part will become apparent to those skilled in the art upon examination of the following and the accompanying drawings or may be learned by production or operation of the examples. The objects and advantages of the present subject matter may be realized and attained by means of the methodologies, instrumentalities and combinations particularly pointed out in the appended claims.

Reference now is made in detail to the examples illustrated in the accompanying drawings and discussed below. Sample configurations will be described with respect to FIGS. 1-5.

FIGS. 1A-1D illustrate examples of a non-invasive blood viscosity monitor, and portions of the environment in which the monitor may be used. In the examples as illustrated, the non-invasive blood viscosity monitor can be a wearable device. The wearing of the non-invasive blood viscosity monitor 100A, 100B, or 100C can allow for mobility that is free and untethered. The wearable non-invasive blood viscosity monitor 100A, 100B, or 100C may include a fixation member 110 and a monitor body 120. The fixation member 110 may detachably affix at least a portion of the blood viscosity monitor to a body part. FIG. 1A illustrates a wrist-worn non-invasive blood viscosity monitor 100A detachably affixed to a wrist. In an example, the wrist-worn non-invasive blood viscosity monitor 100A can be sized and shaped in a form of a wristwatch. In an example, portions of the non-invasive blood viscosity monitor may be incorporated into a smart wearable device, such as a smart watch, a wearable athletic or recreational device, or a sporting gear, among others.

Figure 1C:
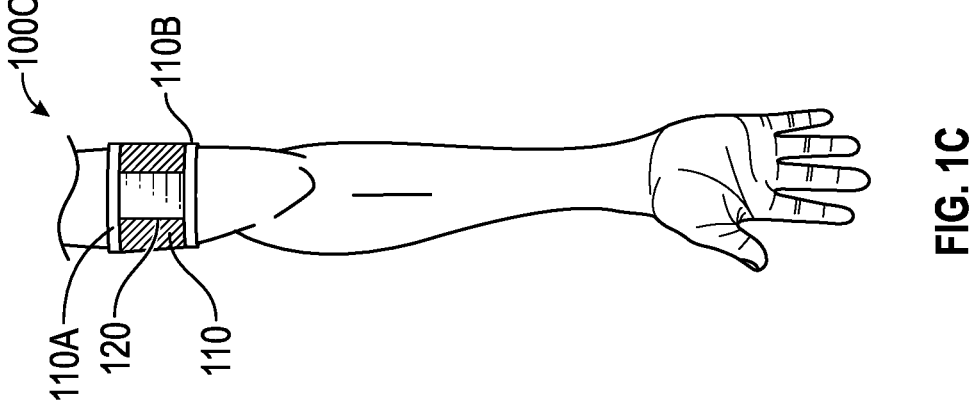
FIG. 1C illustrates an arm-worn non-invasive viscosity monitor.
Figure 1B:
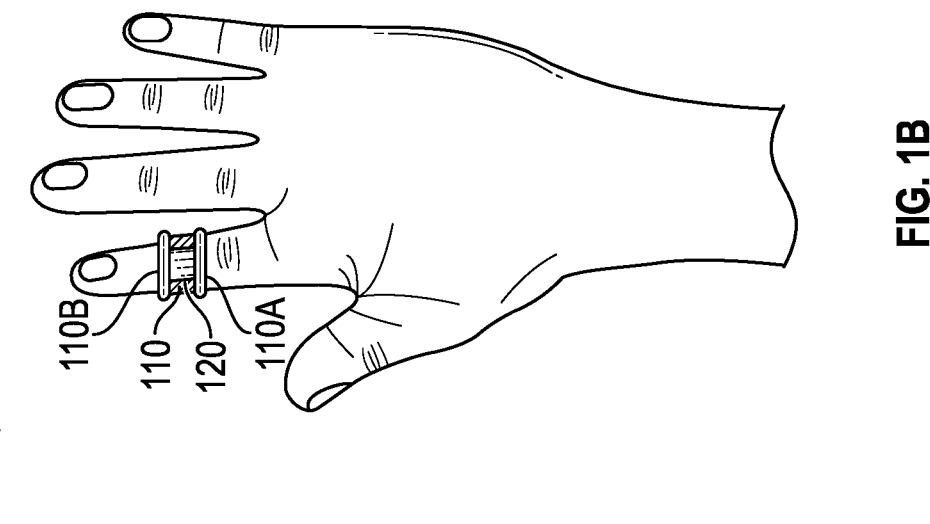
FIG. 1B illustrates a finger-worn non-invasive blood viscosity monitor.

The non-invasive blood viscosity monitor may be configured to detachably affix, such as loop around, other body parts via the fixation member 110. By way of example and not limitation, FIG. 1B illustrates a finger-worn non-invasive blood viscosity monitor 100B, and FIG. 1C illustrates an arm-worn non-invasive viscosity monitor 100C. In other examples, the wearable non-invasive blood viscosity monitor 100A, 100B, or 100C may be sized, shaped, or otherwise configured to be worn in a leg, the chest, the abdomen, the head, or other body parts of the subject with detectable arterial blood flow.

In some examples, the fixation member 110 can be an adjustable strap, band, or cuff enclosed in a sleeve. One or more sensors may be included in the fixation member 110 to measure physiological information correlated to blood flow or blood viscosity. In an example as illustrated in FIGS. 1A-1C, the fixation member 110 may include a first sensor positioned on a first portion 110A and a second sensor positioned at a second portion 110B of the fixation member 110. The first and second portions are spatially apart. In an example, the first portion 110A and the second portion 110B are located at different locations along the length of an artery in the body part (e.g., a wrist, a finger, or an arm) where the non-invasive blood viscosity monitor is attached such that the first and second sensors can sense respectively a sensor signal correlated to blood flow or blood viscosity at respective locations.

Figure 1D:
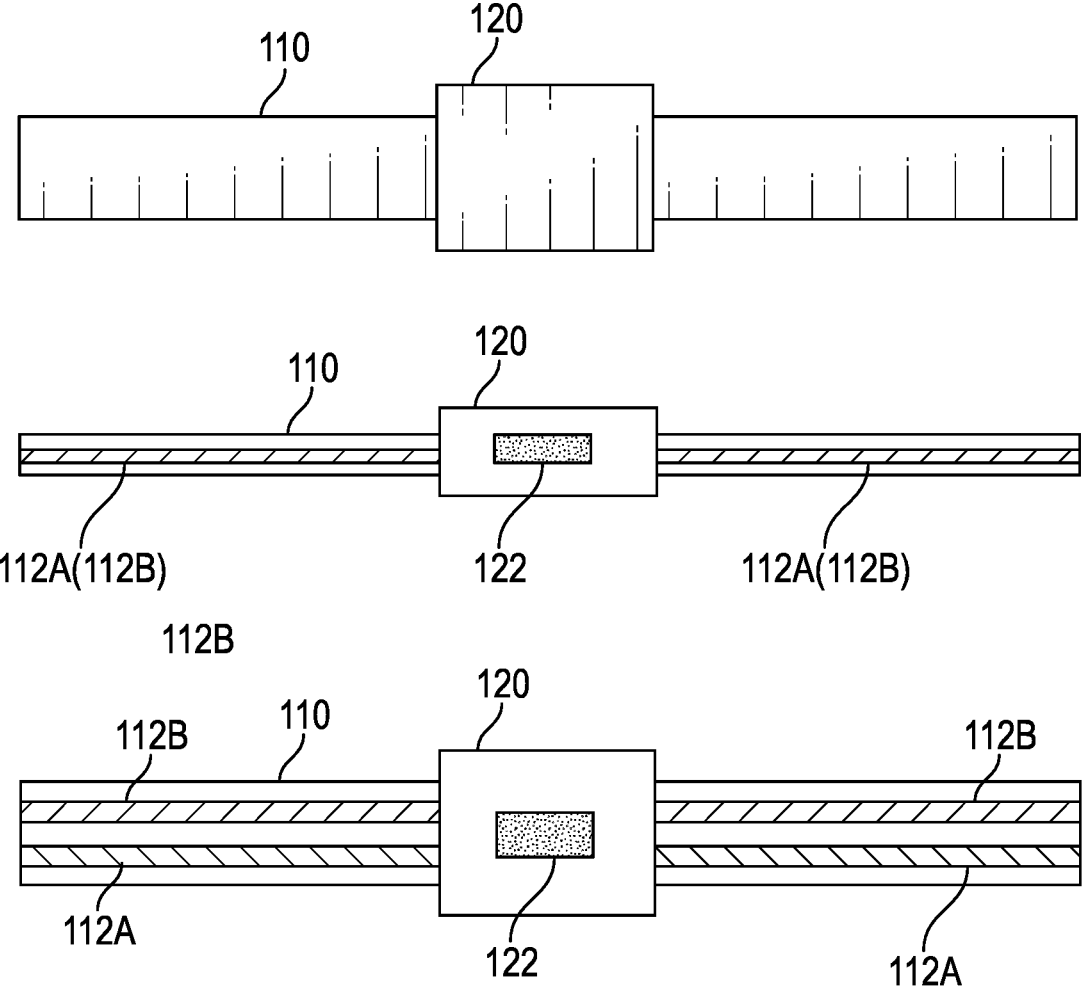
FIG. 1D illustrates a top view, a side view, and a bottom view of a non-invasive blood viscosity monitor of the type illustrated in FIGS. 1A-1C.

FIG. 1D illustrates a top view, a side view, and a bottom view of a non-invasive blood viscosity monitor, such as one of the monitors 100A, 100B, or 100C. In the example as illustrated, the monitor body 120 can be securely attached to the fixation member 110. The fixation member 110 can take a form of an adjustable strap, band, or cuff to loop around or otherwise detachably affix to a body part. By way of example and not limitation, two sets of sensors 112A and 112B can be positioned at different locations of the fixation member 110, such as on a top surface, a bottom surface, or a side surface the fixation member 110. In some examples, one or more of the sensors 112A or 112B can be embedded within the fixation member 110.

The monitor body 120 may include a processor circuit to process the sensor information. In some examples, the monitor body 120 also may include one or more sensors, such as a sensor 122 as illustrated in FIG. 1D, to sense physiological information. The sensor(s) 122 may be located inside the monitor body 120. Additionally, or alternatively, the sensor(s) 122 may be positioned on an exterior of the monitor body 120, such as on a skin-contact surface of the monitor body 120. The processor circuit may pre-process the sensor data sensed by the one or more sensors associated with the monitor body 120 and/or the one or more sensors 112A, 112B on the fixation member 110, and generate a blood viscosity indication, in accordance with various examples as described in this document. The monitor body 120 may include a memory circuit to store the processed physiological data, the viscosity indication, among other physiological information. In some examples, the monitor body 120 may include a display to display the sensor signals and the blood viscosity indication. In an example, portions of the wearable blood viscosity monitor, such as the sensors 122 and a processor for processing the sensor information and generating a blood viscosity indication, may be incorporated into a smart wearable device, such as a smart watch.

The non-invasive blood viscosity monitor 100A, 100B, or 100C may generate a notification to alert the subject or a healthcare professional of abnormally high viscosity or a substantial change in viscosity that exceeds respective predetermined threshold values, such that medical attention may be sought in an emergent fashion. In some examples, the non-invasive blood viscosity monitor 100A, 100B, or 100C may have a communication circuit configured to establish a communication with an external system 150 via a communication link 115. The external system 150 may include a dedicated hardware/software system such as a programming device, a remote server-based system, or a system defined predominantly by software running in the system. By way of example and not limitation, the external system 150 may include a personal computer, a mobile device such as a mobile phone as illustrated in FIG. 1A, or a remote device residing in a medical facility.

The communication link 115 can be a wired or wireless communication link. Examples of the wireless communication link can include inductive telemetry link, a capacitive telemetry link, or a radio-frequency (RF) telemetry link, or wireless telemetry based on, for example, "strong" Bluetooth or IEEE 802.11 wireless fidelity WI-FI® interfacing standards, among others. Other configurations and combinations of patient data source interfacing are possible. Blood viscosity, along with other physiological data, may be transmitted to the external system 150 via the communication link 115. In some examples, the blood viscosity information may be encrypted, along with other security operations, to enhance patient privacy to achieve and maintain regulatory compliance. The blood viscosity information and other patient data may be stored in the external system 150, and/or displayed on a display unit therein. A user may use the external device 150 to control the operation (e.g., adjust the sensor sensitivity or set alerts) of the non-invasive blood viscosity monitor 100A, 100B, or 100C. In some examples, an alert about abnormal viscosity may be generated on the wearable non-invasive blood viscosity monitor 100A, 100B, or 100C and/or on the external system 150. The alert notification may take the form of text, sound, or other forms of warnings to draw attention of the subject or others about the abnormal viscosity.

Figure 2:
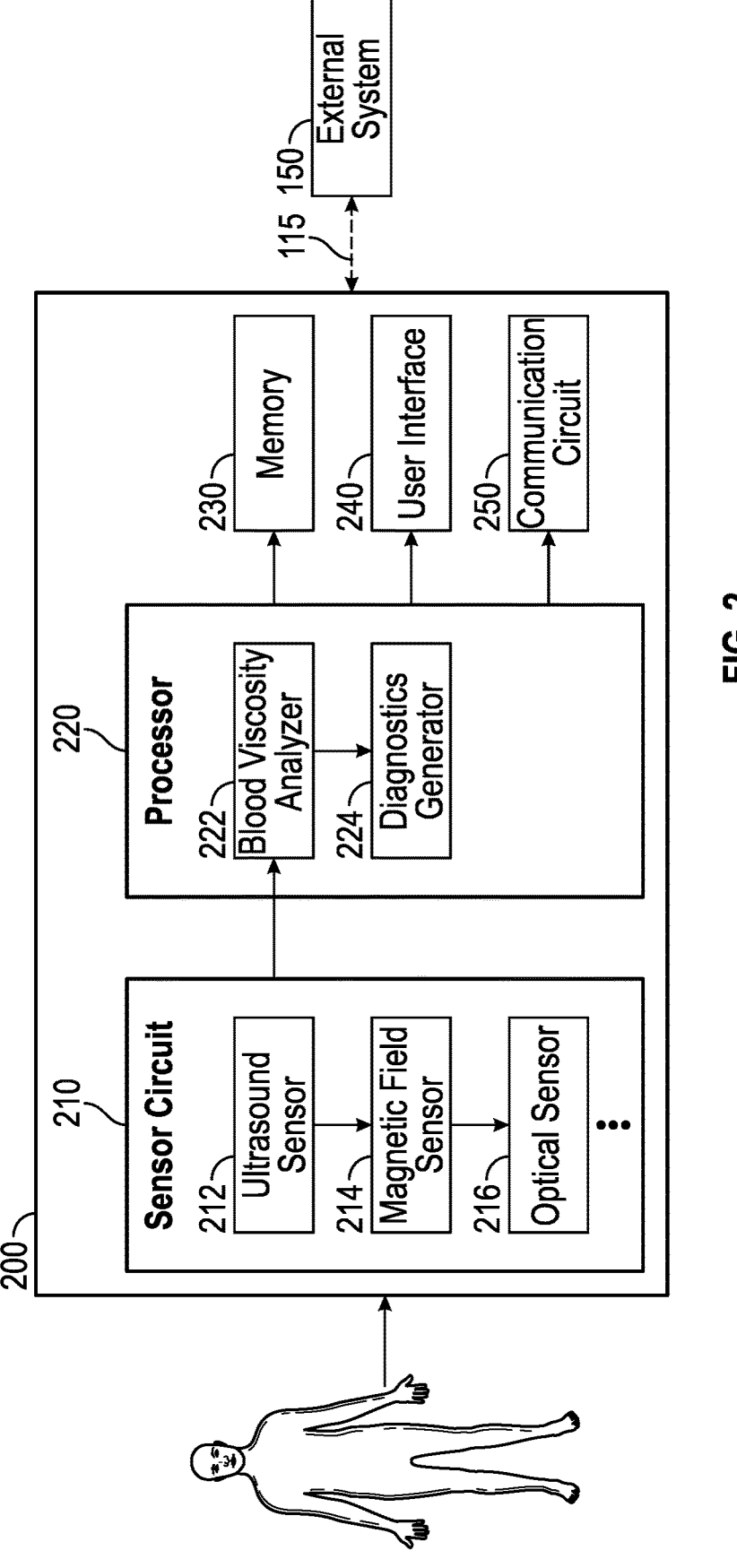
FIG. 2 illustrates a schematic of an example of at least portions of a non-invasive blood viscosity monitor that is an exemplary configuration of any of the wrist-worn, the finger-worn, or the arm-worn blood viscosity monitors shown in FIGS. 1A-1C.

FIG. 2 is a schematic illustrating an example of at least portions of a non-invasive blood viscosity monitor 200, which is an exemplary configuration of any of the wrist-worn, the finger-worn, or the arm-worn blood viscosity monitors 100A-100C shown in FIGS. 1A-1C. The wearable blood viscosity monitor 200 may include a sensor circuit 210, a processor 220, a memory 230, a user interface 240, and a communication system 250.

The sensor circuit 210 may include one or more physiological sensors configured to sense respective physiological information non-invasively from a subject. By way of example and not limitation, sensors included in the sensor circuit 210 may include one or more of an electrochemical sensor, an electrochemi-luminescence sensor, an optical sensor, an electromagnetic sensor, a piezoelectric sensor, a gravimetric sensor, or a pyroelectric sensor, among others. Various parameters corresponding to the high shear/systolic viscosity and parameters corresponding to the low shear/diastolic blood viscosity may be measured. In some examples, the non-invasive blood viscosity monitor 200 may include an imaging sensor configured to generate an image of blood flow and extract image features representing changes in blood flow, which are correlated with, or indicative of, blood viscosity. Examples of the imaging sensors may include sensors employing ultrasound, sound waves, microwaves, radio waves, infrared, magnetic resonance, thermography, or a mini microscope.

Sensor configurations and locations of where the non-invasive blood viscosity monitor, or a portion thereof (e.g., the sensor(s)), may be positioned to acquire physiologic information for blood viscosity assessment may vary. In an example, the locations of the blood viscosity monitor may be dependent upon the sensor modality and parameters to measure. As discussed above with reference to FIGS. 1A-1D, some of the sensors may be detachably and adjustably attached to a strap, band, or cuff of any sort, among other entities securable onto a body part, such as an arm, a wrist, a finger, a leg, the chest, the abdomen, or the head of the subject.

As a non-limiting example shown in FIG. 2, the sensor circuit 210 may include one or more of an ultrasound sensor 212, a magnetic field sensor 214, or an optical sensor 216. The ultrasound sensor 212 may be configured to sense a blood flow rate such as based on an amount of change in frequency of a reflected wave. The ultrasound sensor 212 may include a transmitting element coupled to an ultrasound source and configured to emit an ultrasonic wave to a blood vessel. The ultrasonic wave can be reflected by the flowing blood in the blood vessel. The reflected wave can be received by a receiving element of the ultrasound sensor 212. Since the blood flows in a certain direction, the reflected ultrasonic wave changes in frequency, known as a Doppler shift. Information sensed by the ultrasound sensor 212, such as the frequency change, may be used to calculate blood viscosity.

The magnetic field sensor 214 may include a field application member configured to apply a magnetic field to a target such as a blood vessel. The magnetic field may affect the blood magnetization and cause an orientation change due to the diamagnetism of oxygenated blood. The magnetic field sensor 214 may include a detecting member configured to detect a response to the applied magnetic field at the measurement location. In an example, the magnetic field is a static magnetic field having a constant field strength, such as in a range of approximately 0.1-0.5 Tesla in an example. In another example, the magnetic field is an electromagnetic field, such as radio-frequency (RF) waves, such as in a range of approximately 1 to 20 MHz in an example. The RF waves may be emitted from a portable electronic device, such as a smart phone. Because the RF signal decays at a faster rate when it passes through rapidly flowing arterial blood than slowly flowing viscous blood, the degree of RF signal loss is correlated with varying blood viscosity and can be used to generate an indication of blood viscosity.

Figure 3:
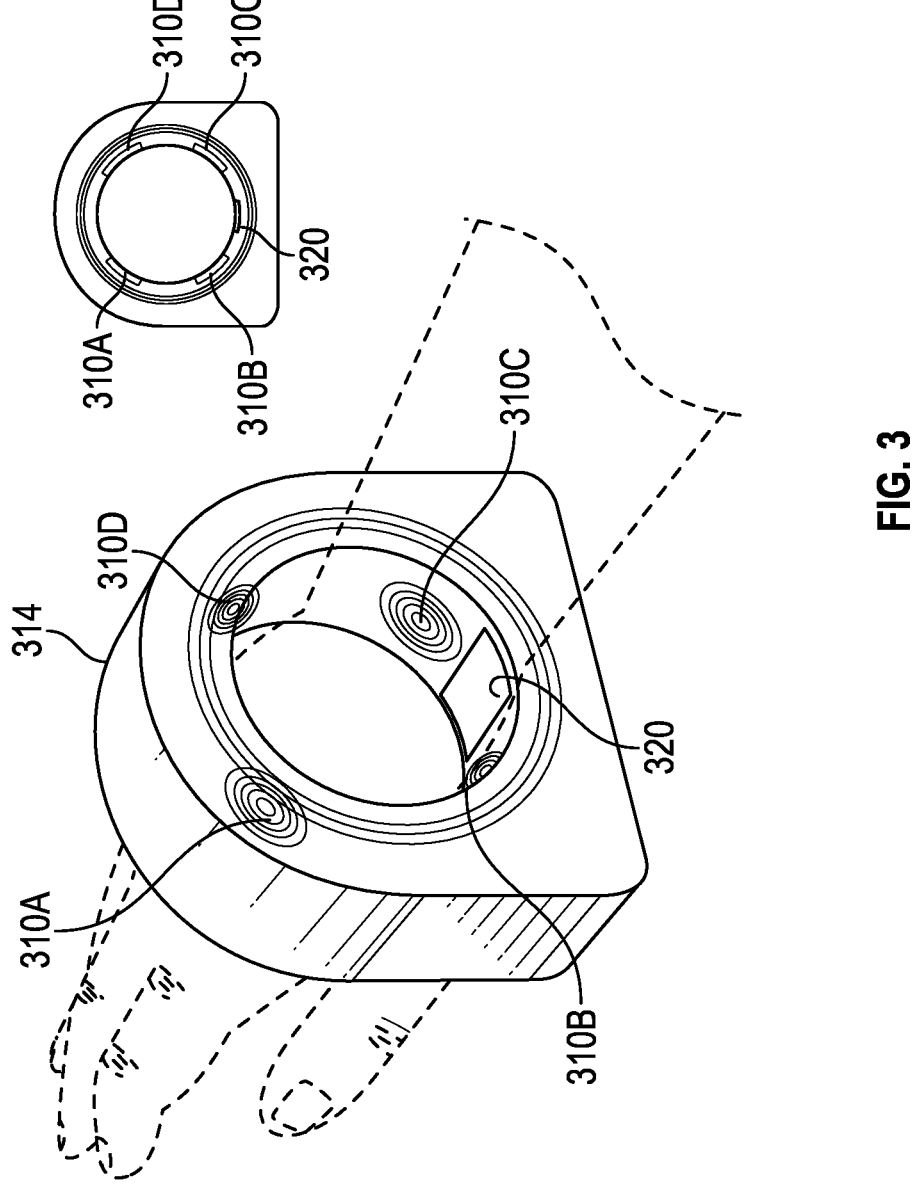
FIG. 3 illustrates an example magnetic field sensor for use in the configuration of FIG. 2.

An example of the magnetic field sensor 214 is shown in FIG. 3. Magnetic field sensor 314 has a ring-shaped portion with a central hole sized and shaped to loop around a wrist or an arm of a subject. The central hole has a substantially circular perimeter. A plurality of field application members, such as 310A-310D as shown, can be circumferentially located at the inner surface of the central hole and along the circular perimeter. The field application members 310A-310D can apply magnetic fields to the wrist or arm portion within the central hole. In some examples, the field application members 310A-310D may apply magnetic field with respective different field strengths. By alternating field application members with different field orientations and/or different field strengths, a varying magnetic field may be created and applied to the blood vessels of the wrist or the arm. A detecting member 320, which may also be circumferentially located within the inner surface of the central hole between two field application members (e.g., between 310B and 310C), can emit light to the blood vessels in the wrist or arm portion, and measure light absorption in the presence of the applied magnetic field. One or more lights with respective different wavelengths may be applied, including, for example, green, red, or infra-red lights. In an example, light absorption may be measured at discrete wavelengths between approximately 380 nm and 960 nm. The magnetic field sensor 214 may, based on the measured light absorption, measure a disturbance in the created magnetic field caused by blood flow. The blood flow rate may then be determined based at least one the applied magnetic field and the magnetic disturbance, as to be discussed in the following.

It has been recognized in the art that blood pulse and flow measurements may be made using the disturbance created by blood flowing through a localized magnetic field. For example, Chee Teck Phua describes in "Novel method of blood pulse and flow measurement using the disturbance created by blood flowing through a localized magnetic field," Other. Univerite Parts-Est, 2012. NNT: 2012PEST1099, a method of blood pulse and flow monitoring termed Modulated Magnetic Signature of Blood (MMSB) where a uniform magnetic field is applied on the skin in a non-invasive manner within close proximity of a major blood vessel (e.g., temple, neck, wrist, and heel) and a Giant-Magneto-Resistance (GMR) based magnetic sensor was demonstrated for use as a wearable device. The uniform magnetic field is generated by a small permanent magnet having a field strength of 0.1-0.2 Tesla. The applied magnetic field creates a uniform magnetic field that encompasses the GMR based magnetic sensor, skin, fabric, and blood vessel. The undisturbed uniform magnetic field produces a fixed DC output voltage from the magnetic field sensor. However, due to the pulsatile nature of blood flow in the arteries, the uniform magnetic field is disturbed periodically, and the GMR based sensor translates the resulting magnetic disturbance into an output electrical voltage.

It is also contemplated that a Tunnel Magneto-Resistance (TMR) effect sensor may be used in place of the GMR based magnetic sensor. TMR sensors utilize a highly sensitive TMR element that implements the magnetoresistance effect, which refers to a change in resistance induced by application of an external magnetic field.

As noted by Phua in the afore-mentioned article, the amplitude of the MMSB pulse (both DC offset and pulsatile waveform) reduces as the occlusion pressure increases. It has been found that the variation in magnetic field in the MMSB method is due to a high magnetization of iron in the blood during slow flow and low magnetization during rapid flow. The direct correlation between the occlusion pressure and the amplitude of the MMSB pulse substantiates the ability of MMSB to measure blood flow qualitatively and quantitatively. Phua further demonstrated that MMSB waveforms may be used to measure Pulse Transit Time (PTT), which may be used with other physical parameters to calculate the patient's Mean Arterial Pressure (MAP). In sample configurations described herein, the MMSB sensors described by Phua may be used as the magnetic field sensor 214 to provide blood flow and PTT data to the processor 220. For example, a small permanent magnet that generates a uniform magnetic field having a field strength of 0.1-0.2 Tesla may be used as one or more of the field application members 310A-310D, while a GMR sensor or TMR sensor is used as the detecting member in the configuration of FIG. 3 for application on the upper arm adjacent the brachial artery or on the wrist adjacent the radial artery, for example.

Referring now back to FIG. 2, the optical sensor 216 may be configured to measure blood velocity using laser Doppler flowmetry (also referred to as laser Doppler velocimetry). The optical sensor 216 may include a first transmitting member coupled to a light source, such as a laser source to emit and transmit a low-power laser beam to a blood vessel. An example of the laser source is a laser diode. In an example, the transmitting member may be located at the sensor tip. The laser beam can penetrate the skin sufficiently to be scattered with a Doppler shift by the red blood cells in the blood stream and return to be concentrated on a second detecting member of the optical sensor 216. The detecting member may sense the reflected light. Because of the blood flow, the intensity of the reflected light fluctuates, the frequency of which is equivalent to the Doppler shift between the incident and reflected light. The blood velocity can be determined based on the Doppler shift.

Other sensors may be used. In an example, a magnetic resonance (MR) sensor may utilize radio-frequency (RF) energy waves by a RF generator such as a smart phone, or other RF emitting portable electronic device. Because the RF signal decays more quickly when it passes through rapidly flowing arterial blood than slowly flowing viscous blood, the degree of RF signal loss is correlated with varying blood viscosity, and thus can be used to generate an indication of blood viscosity.

The sensors included in the non-invasive blood viscosity monitor 200 may have different configurations. In an example, the sensor is a detachable probe configured attach to a mucosal membrane to measure blood viscosity therefrom. In another example, the sensor may include a patch enclosing one or more sensors or coils. In yet another example, the sensor may have a ring-shape portion to interface with a body part, or a disc-shape portion that can be integrated into a portal electronic device such as a smart phone. In yet another example, the sensor may be enclosed in an adjustable strap, band, or cuff adapted to attach to a body part, such as a wrist, an arm, a finger, a leg, the chest, the abdomen, the head, or other body parts of the subject with detectable arterial blood flow. The sensor configuration and location of placement may be optimized for an individual subject to achieve a desired contact with the body part and sensor signal quality.

In some examples, multiple sensors may be placed at respective body locations to produce respective blood viscosity indications. A differential or a set of differentials may be generated from the blood viscosity indications at different body sites to improve accuracy of blood viscosity assessment. For example, a second viscosity measurement by a second sensor may be used to verify the accuracy of a first viscosity measurement by a first sensor being positioned at a different location than the second sensor, the examples of which are illustrated in FIGS. 1A-1D. In some examples, the viscosity measurements by the first and second sensors may be averaged to provide a more robust estimate of the actual blood viscosity.

The processor 220 may be implemented as a part of a microprocessor circuit, which may be a dedicated processor such as a digital signal processor, application specific integrated circuit (ASIC), microprocessor, or other type of processor for processing information including physical activity information. Alternatively, the microprocessor circuit may be a general-purpose processor that may receive and execute a set of instructions of performing the functions, methods, or techniques described herein.

The processor 220 may include circuit sets comprising one or more other circuits or sub-circuits, including, for example, a blood viscosity analyzer 222 and a diagnostics generator 224. These circuits or sub-circuits may, individually or in combination, perform the functions, methods or techniques described herein. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

The blood viscosity analyzer 222 may determine a blood flow rate using the reflected wave sensed by the ultrasound sensors 212, such as the amount of frequency shift due to Doppler effect, and calculate the blood viscosity using the determined blood flow rate. Additionally, or alternatively, the blood viscosity analyzer 222 may determine the blood flow rate using the response to the applied magnetic field, such as based on an amount of RF signal loss between the received RF signal strength and the transmitted RF signal strength. In some examples, the transmitting member of the magnetic field sensor 214 may produce magnetic fields with different field strengths and applied at different orientations, as discussed above with reference to FIG. 3. The receiving member of the magnetic field sensor 214 may sense a disturbance in the created magnetic field caused by blood flow. The blood viscosity analyzer 222 may determine a blood flow rate using the magnetic field and the measured magnetic disturbance. Additionally, or alternatively, the blood viscosity analyzer 222 may determine the blood flow rate based on the intensity of the reflected light fluctuates sensed by the optical sensor 216, the frequency of which is equivalent to the Doppler shift between the incident and reflected light.

The blood flow rate is inversely proportional to blood viscosity, and directly proportional to a blood pressure (BP) difference. Mathematically, blood flow is described by Darcy's law and approximated by the Hagen-Poiseuille equation. That is, $Q=(\pi R^4/8L)*\Delta P/\eta$, where Q is the blood flow rate, $\Delta P$ are the BP difference measured along the blood vessel at two locations with a distance L, $\eta$ is the viscosity, and R is the radius of blood vessel. For a given BP difference along a blood vessel, if blood viscosity increases, then the total peripheral resistance (TPR) will necessarily increase, thereby reducing blood flow. Conversely, when viscosity decreases, blood flow and perfusion will increase. In some examples, the processor 220 may receive blood pressure difference and information about vascular geometry (e.g., diameter of the blood vessel, and distance between two locations along the blood vessel where the BP difference is measured), and the blood viscosity analyzer 222 may determine the blood viscosity using the blood flow determined based on one or more of the ultrasound sensor signal, the magnetic field sensor signal, or the optical sensor signal, along with the received BP difference and the vascular geometry information. In some examples, the non-invasive blood viscosity monitor 200 may include a wearable pressure sensor configured to sense the BP difference. The wearable pressure sensor may be located at an adjustable strap, band, or cuff of the fixation member 110, or on an exterior surface of or embedded in the interior of the monitor body 120, of the wearable non-invasive blood viscosity monitor 100A, 100B, or 100C. In some examples, under an assumption of a substantially constant vascular geometry, the blood viscosity analyzer 222 may determine a change in viscosity from a reference viscosity (e.g., corresponding to a baseline condition of the subject) based on a change in blood flow from a reference flow level corresponding to the baseline condition of the subject.

In some examples, the blood viscosity analyzer 222 may include a sensor fusion module configured to calculate a composite blood viscosity indication using a combination of two or more viscosity indications respectively determined based on the ultrasound sensor signal, the magnetic field sensor signal, or the optical sensor signal.

The non-invasive blood viscosity monitor 200 may be programmed to monitor patient viscosity continuously or periodically, such as in a chronic setting. The diagnostics generator 224 may generate diagnostics, such as a risk of stroke, based on the blood viscosity calculated by the blood viscosity analyzer 222. In some examples, the diagnostics generator 224 may screen patients at risk of undiagnosed diseases or a medical event, such as a stroke, a heart attack, diabetes, blood cell cancers, sickle cell anemia, or inflammatory states, among others, based on the monitored blood viscosity or a change in blood viscosity from a reference level. In some examples, the diagnostics generator 224 may use the blood viscosity indication to screen patients of a dysfunctional state, such as dysfunctions of blood entities. The non-invasive blood viscosity monitor 200 may generate a notification of an elevated viscosity or alert a clinician of an elevated risk of an adverse event, such as a cerebrovascular accident (stroke) or myocardial infarction (heart attack). In yet another example, the blood viscosity indication may be used to generate an indicator for further tests, such as diagnostic assays which evaluate patient risk or occurrence of cardiovascular or cerebrovascular events. The generated diagnostics and notifications may be displayed locally on the user interface 240 and/or may be transmitted to external system 150 for display to a user or clinician.

In another example, the blood viscosity indication may be used to generate one or more medical diagnostics. In some examples, the blood viscosity monitor can include a cardiac sensor configured to sense systole and diastole in a cardiac cycle, and the processor can generate one or more of an indication of systolic viscosity during the sensed systole, or an indication of diastolic viscosity during the sensed diastole. Various parameters can be determined respectively during systole (corresponding to the high shear, systolic viscosity) and during diastole (corresponding to the low shear, diastolic blood viscosity).

Additional diagnostics and parameters relative to coagulation or clotting may be generated based on the non-invasive blood viscosity monitoring. Blood viscosity at specific shear rates is correlated with points in the clotting cascade and coagulation pathway. The time to gel point (TGP), which represents the time for blood to change from a fluid state to solid state, is dependent on shear rate changes. In an example, the blood viscosity indication generated by the non-invasive blood viscosity monitor may be used to diagnose dysfunction of the coagulation pathways, or to detect acute clot formation.

The blood viscosity and/or the diagnostics generated by the processor may be stored in the memory 230. Other information, including sensor signals sensed by the sensor circuit 210, may also be stored in the memory 230. The blood viscosity and/or the diagnostics stored in the memory 230 may be retrieved by a different device or a different process.

The processor 220 may be communicatively coupled to the user interface 240. Various information, including blood viscosity and/or the diagnostics, may be presented to a user such as via a display on the user interface 240. In an example, the user interface 240 may be integrated into the wearable monitor such as the non-invasive blood viscosity monitor 100A, 100B, or 100C. In some examples, the user interface 240 may be a part of the external system 150, such as a mobile phone.

In an example, the user interface 240 may generate an alert to warn the subject or a healthcare professional of abnormal blood viscosity level and in some instances, an elevated risk of an adverse event such as stroke or heart attack. This allows the subject to take immediate actions proactively to avoid a potential hazardous or unsafe circumstances, and/or allows a healthcare professional to provide timely care to the subject.

The communication circuit 250 may be operably in communication with the external system 150 via the communication link 115, as described above in reference to FIG. 1A. In an example, the external system 150 may include a mobile computing device, such as a smart phone. The mobile device can be configured to generate the indication of blood viscosity or the diagnostic, or to provide the diagnostic to a user.

Those skilled in the art will appreciate that there are advantages and disadvantages to the use of ultrasound sensors 212, magnetic field sensors 214, optical sensors 216, and other sensors in different environments. For example, magnetic field sensors 214 may be preferred in those situations where it is difficult to maintain the optical sensor 216 in contact with the skin. Conversely, optical field sensors 216 may be preferred in those cases where there is magnetic interference or for those situations where the magnetic field sensor 214, ultrasound sensor 212 or other sensor is not suitable for the available form factor.

Figure 4:
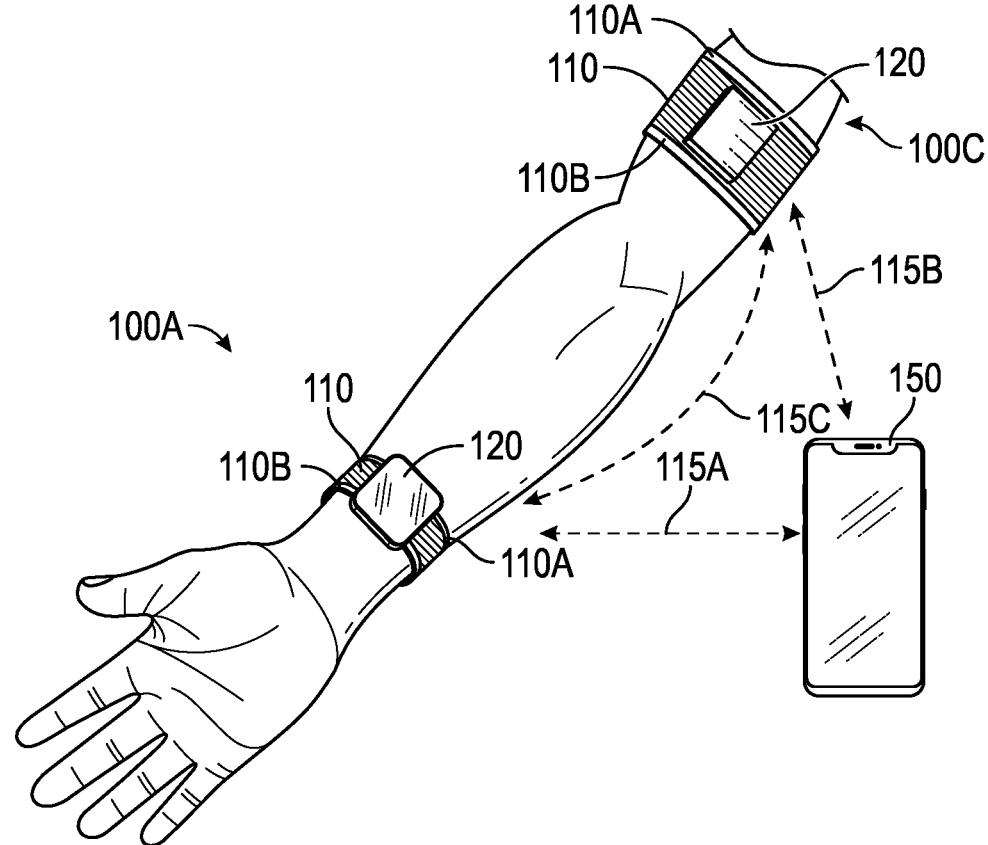
FIG. 4 illustrates a viscosity monitor including a magnetic field sensing device and an optical sensing device incorporated into the wrist-worn non-invasive blood viscosity monitor of FIG. 1A, into the arm-worn non-invasive blood viscosity monitor of FIG. 1C, or one in each viscosity monitor.

Accordingly, further configurations are provided where any combination of the ultrasound sensors 212, magnetic field sensors 214, the optical sensors 216, and other sensors are available. By way of example, FIG. 4 illustrates a configuration of a non-invasive blood viscosity monitor including wrist-worn and arm-worn non-invasive blood viscosity sensor devices 100A, 100C adapted to determine blood viscosity. In a sample configuration, the arm-worn non-invasive viscosity sensor device 110C may include magnetic field sensor 214 for measuring blood flow and blood pressure. Also, the magnetic field sensor 214 may be adapted to measure impedance in the blood vessels, from which viscosity may be directly determined. Other sensing devices of the type mentioned above also may be provided in the arm-worn non-invasive viscosity sensor device 110C. The measurements are communicated to a processing communication circuit configured to establish a communication with an external system 150 via a communication link 115B. As noted above, the external system 150 may include a dedicated hardware/software system such as a programming device, a remote server-based system, or a system defined predominantly by software running in the system. By way of example and not limitation, the external system 150 may include a personal computer, a mobile device such as a mobile phone as illustrated in FIG. 3, or a remote device residing in a medical facility. Alternatively, or additionally, the arm-worn non-invasive viscosity sensor device 100C may include a processing communication circuit 250 that is configured to establish a communication with the wrist-worn non-invasive sensor device 100A via a communication link 115C.

In a sample configuration, the wrist-worn non-invasive sensor device 100A may include optical sensor 216 for also measuring blood flow and blood pressure. The blood flow, blood pressure differential, and/or viscosity measurements by the arm-worn non-invasive viscosity sensor device 100C may be used to verify the accuracy of the blood flow, blood pressure differential, and/or viscosity measurements by the wrist-worn non-invasive sensor device 100A and vice-versa. Also, the blood flow, blood pressure differential, and/or viscosity measurements by the respective sensors may be averaged to provide a more robust estimate of the actual blood viscosity. Additionally, one sensor may be given priority over the other based on which sensor provides the best reading (most reliable data for each modality, the given context, least noisy signal, etc.) in the viscosity calculation. Different modalities may include in-patient or clinical setting while another modality may be out-patient. The inputs to the equations for calculation of viscosity or other calculated values may be mixed and matched depending upon the modalities and the reliability of the data. If the respective inputs are provided to a processor 220 of the wearable device, the wearable device may become a universal processor for the different measured values and provide a display for the medically relevant data that may be calculated from the different measured values.

It will also be appreciated that the blood flow measurements taken by the arm-worn non-invasive viscosity sensor device 100C and the wrist-worn non-invasive viscosity sensor device 100A may be compared to establish differences in blood flow between the brachial artery of the upper arm and the radial artery at the wrist. The differences may be used to identify blockages, to calibrate the sensors, and the like. The design of FIG. 4 is desirable as the magnetic components in the arm-worn non-invasive viscosity sensor device 100C are sufficiently separated from the optical components in the wrist-worn non-invasive viscosity sensor device 100A to avoid interference.

Alternatively, the magnetic field sensor 214 and the optical sensor 216 both may be included in the wrist-worn non-invasive sensor device 100A or both may be included in the arm-worn non-invasive sensor device 100C so long as low profile magnetic shielding is provided between the magnetic field sensor 214 and the optical sensor 216 to minimize interference. In such a configuration, the optical sensor 216 may be disposed on the radial side of the wrist (110A) while the magnetic field sensor 214 is disposed on the ulnar side of the wrist (110B). Conversely, the magnetic sensor field sensing device 214 and the optical sensing device 216 both may be included in the arm-worn non-invasive sensor device 100C adjacent the brachial artery on opposite sides of the arm so long as low profile magnetic shielding is provided between the magnetic field sensor 214 and the optical sensor 216 to minimize interference. The same magnetic field isolation would be needed for separating the ultrasound sensor components and any other sensor components from the magnetic sensor components.

In each of these examples, the blood flow rate Q may be determined by one or both of the magnetic field sensor 214 and the optical sensor 216 and the blood pressure difference $\Delta P$ between systole and diastole measured along the blood vessel at two locations separated by a distance L may be used to calculate the viscosity $\eta$ where $\eta=(\pi R^4/8L)^*\Delta P/Q$, where R is the radius of blood vessel. Of course, where the measurements are taken using the arm-worn non-invasive sensor device 100C and the wrist-worn non-invasive sensor device 100A, measurements for the distance L between the arm-worn non-invasive sensor device 100C and the wrist-worn non-invasive sensor device 100A will need to be obtained and the radius R will need to be obtained for both the brachial and the radial arteries to properly calibrate the respective readings by comparing waveforms or using carbon nanotube (CNT) deflection comparisons. A very small flexible ultrasound sensor may be used to measure vessel geometry, blood pressure, and MPG (a magnetic version of plethysmograph) based on the MMSB, but with a Hall sensor. The measured Q data and the measured $\Delta P$ data are provided to the processor 150 or a processor 220 of the monitor body 120 for calculation of the viscosity $\eta$ irrespective of from which type of sensor obtained the data and irrespective of the modality from which the data was obtained.

In any of these configurations, heat dissipation devices may be used to dissipate the heat generated by the electronic components. For example, dielectric nanoantennas may be used for heat dissipation. The tuning of nano antenna frequencies may be dynamic and remotely controlled.

As noted above, the data captured by the magnetic field sensor 214, provided as, for example, sensor 112B (FIG. 1D), may be sent to the processor 220 of the monitor body 120 for processing. On the other hand, a measured voltage representing displacement information from the magnetic field sensor 214 may be provided to a carbon nanotube (CNT) sensor of the optical sensor 216, provided as, for example, sensor 112A (FIG. 1D). The CNT sensor of the optical sensor 216 would be deflected by the received voltages to allow light to pass through openings. The sensed light collected by the optical sensor 216 that has passed through the openings would be processed to convert the magnetic field data to optical data representing phase shifts in the applied light data collected by the optical sensor 216. This data would be representative of the "drag force" response to pulse pressure applied to the CNT sensor. As such, if the CNT is thought of as cantilevered segments, then each segment on the Y-axis also represents voltages. The respective differential drag forces at position $\Delta y$ would be proportionate to the resistance to flow at the associated radial level in the blood vessel. From $\Delta y$, the resistance to flow at the boundary layer may be calculated. Alternatively, the phase shifts may be measured with wave plates. In such a case, as the energy level changes, the lag, phase shift of the perpendicular component of a split beam against the axially optical component changes as well.

In operation, the magnetic field sensor 112B would capture the magnetic field data in the form of voltages representing shear ("drag") force in the blood and provide the voltages to a processor (e.g., processor 150 or processor 220 of the monitor body 120) for processing. The voltages may also be provided to the CNT sensor to cause an angle of displacement of the carbon nanotubes representing strain. The displacement data may be processed with the optical data by the processor 150 or processor 220 of the monitor body 120 for calculation of the strain and hence the viscosity.

Rostami et al. describe in "Fabrication of optical magnetic mirrors using bent and mushroom-like carbon nanotubes" in Carbon 48 (2010), pp. 3659-3666, the fabrication of an optical magnetic mirror using CNT-based 3-dimensional nano-structures. Bent carbon nanotubes (CNTs) with a controllable bending angle were obtained by changing the direction of the electrical field of the applied plasma. Mushroom-like carbon nanostructures with a high-impedance surface were obtained by deposition of a gold layer on vertically grown CNTs using a sputtering system. The drag force, the blood's resistance to flow, may be shown mechanically from the deflection of the CNT. Optically, that same resistance is a change of the energy level as there is a phase shift as the energy level of the impedance surface changes. This means that a signal correlated to the zero phase shift can no longer be present. Conversely, if the signal is not present, then its presence can trigger an alarm. Phase differences between the incident beam on the surfaces and the beam reflected from the surfaces were found to be almost zero by Rostami et al., indicating that the direction of the electric field had not been changed upon reflection but instead reversed the direction of the magnetic field. To provide a magnetic mirror in the range of optical waves, sculptured surfaces with nanoscale patterns are created that are compatible with the optical wavelength. Rostami et al. further observed that the phase change of the reflected electrical field is a function of the wavelength for different heights and spacings of the nanostructures. The phase change becomes zero for wavelengths in the optical range. An advantage of optical magnetic mirrors (OMMs) is that a transverse-electric dipole placed close to the mirror surface is located at an antinode of the incident plus reflected electric field and thus can absorb and emit efficiently, which allows for smaller and more efficient antennas and circuits. Thus, even better precision can be achieved and that even smaller bandwidths may be provided for tuning capability, representing the energy levels of the blood, can be achieved using OMMs. The bandwidths of these OMMs and of these impedance surfaces can measure energies in the IR and optical range, and when blood energy level is in resonance with a discrete bandwidth, the OMM property of the reflecting beam with zero phase shift may be used as a signal to represent discrete viscosity values. Also, CNTs have been shown to be practically applied for tactile and shear force sensing for monitoring fluid flows. Fluid velocity, drag force, and CNT deflection has been shown to be a function of the heights of the CNTs (see, e.g., Chi-Nung Ni, "Electronic, Optical, and Mechanical Characterization of Zero- and One-Dimensional Nanostructures," PHD Dissertation, University of California, San Diego, 2008).

As an extension of OMMs, patterned grids with varying size holes and density, so-called CNT forests, which have periodic nano textures matching the imprinted patterns, may be used to vary the effective CNT density and the resulting refractive index. The textured base density tuning enables growth thickness vertically aligned CNT films with prescribed anisotropic optical properties. The effective density of CNTs in macroscale films may be modulated by sub-micrometer patterning of the CNT growth catalyst using nano imprint lithography (NIL). The NIL-patterned catalysts may result in CNT forests with uniform texture on a length scale smaller than visible light, and the influence of the pattern on effective density may be assessed using optical attenuation. Also, the average density of the CNT forest may be derived by treating the CNT forest as an effective medium of individual absorbers. As described Park et al. in "Modulation of the effective density and refractive index of carbon nanotube forests via nanoimprint lithography," (www.sciencedirect.com/science/article/pii/S0008622317311934), the Beer-Lambert law may be used to calculate the average density of the NIL-patterned CNT forests as $T = I/I_0 = e^{-\mu l}$, where T is the transmittance which is a ratio of the intensity of transmitted light (I) over intensity of incident light ($I_0$), $\mu$ is the attenuation coefficient, and I is the path length. By using identical samples, the path length may be fixed in this equation, and hence the product of $\mu$ and l can represent each sample's optical attenuation.

It has been shown in the prior art that there is a high correlation between impedance and viscosity (see, e.g., Pop et al. in "On-Line Electrical Impedance Measurement for Monitoring Blood Viscosity During On-Pump Heart Surgery," Eur Surg Res 2004; 36:259-265. An equivalent circuit of a high impedance surface can be modeled by an equivalent circuit. The resonance frequency of the high impedance surface depends on the surface parameters by the equation: Impedance=1/square root of inductance and capacitance. These variables depend on length and surface porosity respectively (length—inductance, surface porosity—capacitance). Rostami et al. show the phase change of the fabricated nano structured high impedance surface as a function of wavelength for different spacings between the nanostructures. The impedance may be solved for optically. Changes in the spacing and height of the nanostructures in the planar and vertical directions affect frequency.

The complex refractive index of blood may be is defined as $n = n(r) + ik$ for the real refractive index n, which describes energy storage, and the imaginary refractive index k, which describes energy dissipation and specifies the extinction coefficient. Thus, a laser seeing changes in refractive index corresponds to the phase shifts of the OMMs and the resonance signal being elicited from one bandwidth of an OMM to another. In other words, the phase shifts with the change of energy level due to change in viscosity, which can be used to tune the resonance frequencies of all the OMMs such that a processor may interpret the presence of zero phase shift at a certain resonance frequency as an alarm, or the lack of a signal could in other instances elicit the alarm. Such devices may be used to as the afore-mentioned CNTs to provide the displacement data representative of the strain and hence the viscosity in the adjacent arteries.

System Configuration

Techniques described herein may be used with one or more of the computer systems described herein or with one or more other systems. For example, the various procedures described herein may be implemented with hardware or software, or a combination of both. For example, at least one of the processor, memory, storage, output device(s), input device(s), or communication connections discussed below can each be at least a portion of one or more hardware components. Dedicated hardware logic components can be constructed to implement at least a portion of one or more of the techniques described herein. For example, and without limitation, such hardware logic components may include Field-programmable Gate Arrays (FPGAs), Program-specific Integrated Circuits (ASICs), Program-specific Standard Products (ASSPs), System-on-a-chip systems (SOCs), Complex Programmable Logic Devices (CPLDs), etc. Applications that may include the apparatus and systems of various aspects can broadly include a variety of electronic and computer systems. Techniques may be implemented using two or more specific interconnected hardware modules or devices with related control and data signals that can be communicated between and through the modules, or as portions of an application-specific integrated circuit. Additionally, the techniques described herein may be implemented by software programs executable by a computer system. As an example, implementations can include distributed processing, component/object distributed processing, and parallel processing. Moreover, virtual computer system processing can be constructed to implement one or more of the techniques or functionality, as described herein.

Figure 5:
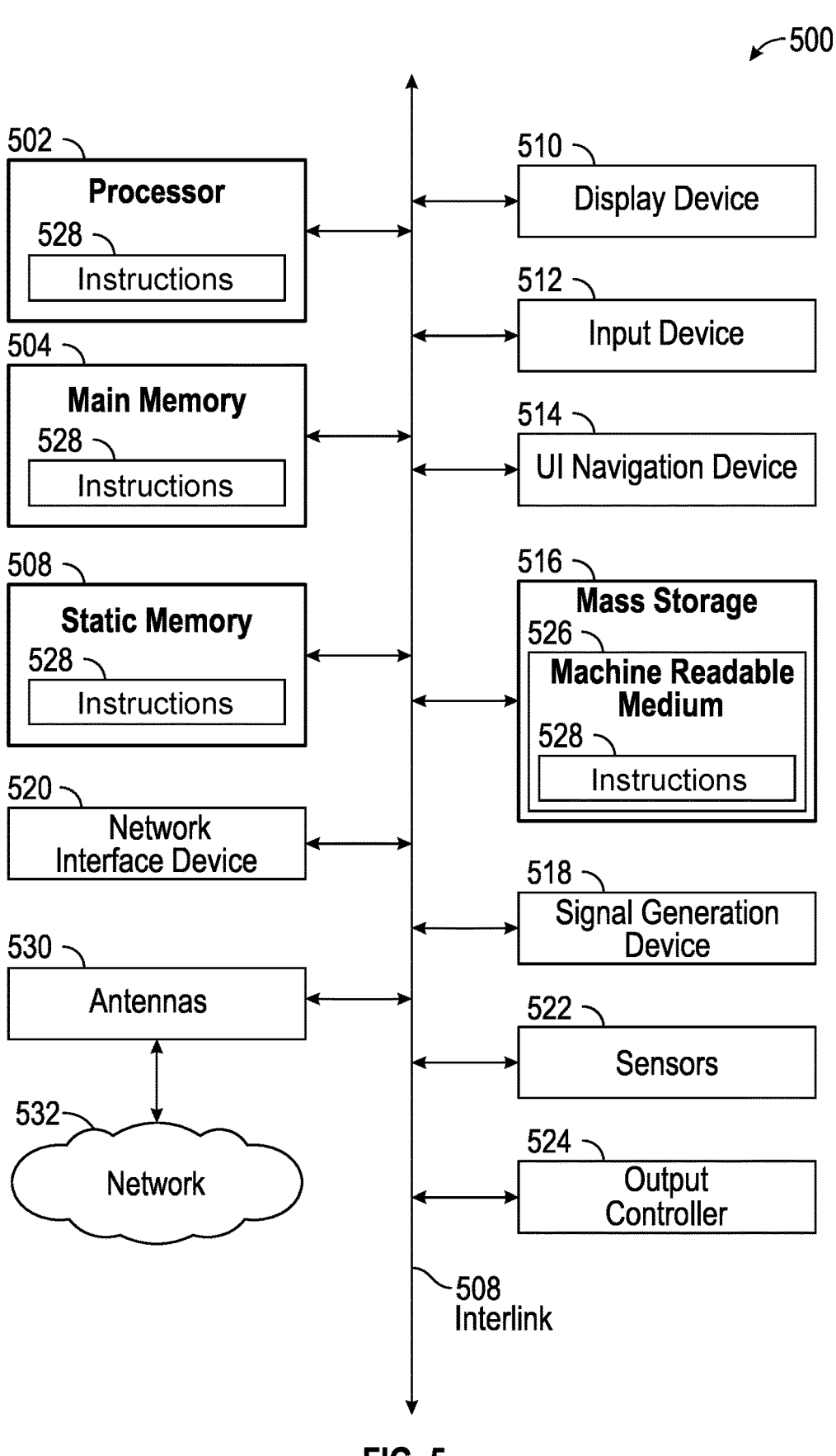
FIG. 5 illustrates an example configuration of a computer system adapted to implement the computer processing in accordance with the systems and methods described herein.

By way of example, FIG. 5 illustrates a sample configuration of a computer system 500 adapted to implement the processing circuit 220 or 150 in accordance with the systems and methods described herein. In particular, FIG. 5 illustrates a block diagram of an example of a machine 500 upon which one or more configurations may be implemented. In alternative configurations, the machine 500 may operate as a standalone device or may be connected (e.g., networked) to other machines. In a networked deployment, the machine 500 may operate in the capacity of a server machine, a client machine, or both in server-client network environments. In an example, the machine 500 may act as a peer machine in peer-to-peer (P2P) (or other distributed) network environment. In sample configurations, the machine 500 may be a personal computer (PC), a tablet PC, a set-top box (STB), a personal digital assistant (PDA), a mobile telephone, a smart phone, a web appliance, a server, a network router, switch or bridge, or any machine capable of executing instructions (sequential or otherwise) that specify actions to be taken by that machine. For example, machine 500 may serve as a workstation, a front-end server, or a back-end server of a communication system. Machine 500 may implement the methods described herein by running the software used to implement the processing circuitry described herein. Further, while only a single machine 500 is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate on, processors, logic, or a number of components, modules, or mechanisms (herein "modules"). Modules are tangible entities (e.g., hardware) capable of performing specified operations and may be configured or arranged in a certain manner. In an example, circuits may be arranged (e.g., internally or with respect to external entities such as other circuits) in a specified manner as a module. In an example, the whole or part of one or more computer systems (e.g., a standalone, client or server computer system) or one or more hardware processors may be configured by firmware or software (e.g., instructions, an application portion, or an application) as a module that operates to perform specified operations. In an example, the software may reside on a machine readable medium. The software, when executed by the underlying hardware of the module, causes the hardware to perform the specified operations.

Accordingly, the term "module" is understood to encompass at least one of a tangible hardware or software entity, be that an entity that is physically constructed, specifically configured (e.g., hardwired), or temporarily (e.g., transitorily) configured (e.g., programmed) to operate in a specified manner or to perform part or all of any operation described herein. Considering examples in which modules are temporarily configured, each of the modules need not be instantiated at any one moment in time. For example, where the modules comprise a general-purpose hardware processor configured using software, the general-purpose hardware processor may be configured as respective different modules at different times. Software may accordingly configure a hardware processor, for example, to constitute a particular module at one instance of time and to constitute a different module at a different instance of time.

Machine (e.g., computer system) 500 may include a hardware processor 502 (e.g., a central processing unit (CPU), a graphics processing unit (GPU), a hardware processor core, or any combination thereof), a main memory 504 and a static memory 506, some or all of which may communicate with each other via an interlink (e.g., bus) 508. The machine 500 may further include a display device 510 (shown as a video display), an alphanumeric input device 512 (e.g., a keyboard), and a user interface (UI) navigation device 514 (e.g., a mouse). In an example, the display device 510, input device 512 and UI navigation device 514 may be a touch screen display. The machine 500 may additionally include a mass storage device (e.g., drive unit) 516, a signal generation device 518 (e.g., a speaker), a network interface device 520, and one or more sensors 522. Example sensors 522 include one or more of a global positioning system (GPS) sensor, compass, accelerometer, temperature, light, camera, video camera, sensors of physical states or positions, pressure sensors, fingerprint sensors, retina scanners, or other sensors. The machine 500 may include an output controller 524, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The mass storage device 516 may include a machine readable medium 526 on which is stored one or more sets of data structures or instructions 528 (e.g., software) embodying or utilized by any one or more of the techniques or functions described herein. The instructions 528 may also reside, completely or at least partially, within the main memory 504, within static memory 506, or within the hardware processor 502 during execution thereof by the machine 500. In an example, one or any combination of the hardware processor 502, the main memory 504, the static memory 506, or the mass storage device 516 may constitute machine readable media.

While the machine readable medium 526 is illustrated as a single medium, the term "machine readable medium" may include a single medium or multiple media (e.g., at least one of a centralized or distributed database, or associated caches and servers) configured to store the one or more instructions 528. The term "machine readable medium" may include any medium that is capable of storing, encoding, or carrying instructions for execution by the machine 500 and that cause the machine 500 to perform any one or more of the techniques of the present disclosure, or that is capable of storing, encoding, or carrying data structures used by or associated with such instructions. Non-limiting machine readable medium examples may include solid-state memories, and optical and magnetic media. Specific examples of machine readable media may include non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; Random Access Memory (RAM); Solid State Drives (SSD); and CD-ROM and DVD-ROM disks. In some examples, machine readable media may include non-transitory machine-readable media. In some examples, machine readable media may include machine readable media that is not a transitory propagating signal.

The instructions 528 may further be transmitted or received over communications network 532 using a transmission medium via the network interface device 520. The machine 500 may communicate with one or more other machines utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®), IEEE 802.15.4 family of standards, a Long Term Evolution (LTE) family of standards, a Universal Mobile Telecommunications System (UMTS) family of standards, peer-to-peer (P2P) networks, among others. In an example, the network interface device 520 may include one or more physical jacks (e.g., Ethernet, coaxial, or phone jacks) or one or more antennas 530 to connect to the communications network 532. In an example, the network interface device 520 may include a plurality of antennas 530 to wirelessly communicate using at least one of single-input multiple-output (SIMO), multiple-input multiple-output (MIMO), or multiple-input single-output (MISO) techniques. In some examples, the network interface device 520 may wirelessly communicate using Multiple User MIMO techniques.

The features and flow charts described herein can be embodied in on one or more methods as method steps or in one more applications as described previously. According to some configurations, an "application" or "applications" are program(s) that execute functions defined in the programs.

Various programming languages can be employed to generate one or more of the applications, structured in a variety of manners, such as object-oriented programming languages (e.g., Objective-C, Java, or C++) or procedural programming languages (e.g., C or assembly language). In a specific example, a third party application (e.g., an application developed using the ANDROID™ or IOS™ software development kit (SDK) by an entity other than the vendor of the particular platform) may be mobile software running on a mobile operating system such as IOS™, ANDROID™, WINDOWS® Phone, or another mobile operating systems. In this example, the third party application can invoke API calls provided by the operating system to facilitate functionality described herein. The applications can be stored in any type of computer readable medium or computer storage device and be executed by one or more general purpose computers. In addition, the methods and processes disclosed herein can alternatively be embodied in specialized computer hardware or an application specific integrated circuit (ASIC), field programmable gate array (FPGA) or a complex programmable logic device (CPLD).

Program aspects of the technology may be thought of as "products" or "articles of manufacture" typically in the form of at least one of executable code or associated data that is carried on or embodied in a type of machine readable medium. For example, programming code could include code for the touch sensor or other functions described herein. "Storage" type media include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another. Thus, another type of media that may bear the programming, media content or meta-data files includes optical, electrical, and electromagnetic waves, such as used across physical interfaces between local devices, through wired and optical landline networks and over various air-links. The physical elements that carry such waves, such as wired or wireless links, optical links, or the like, also may be considered as media bearing the software. As used herein, unless restricted to "non-transitory", "tangible", or "storage" media, terms such as computer or machine "readable medium" refer to any medium that participates in providing instructions or data to a processor for execution.

Hence, a machine readable medium may take many forms of tangible storage medium. Non-volatile storage media include, for example, optical or magnetic disks, such as any of the storage devices in any computer(s) or the like, such as may be used to implement the client device, media gateway, transcoder, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a PROM and EPROM, a FLASH-EPROM, any other memory chip or cartridge, a carrier wave transporting data or instructions, cables or links transporting such a carrier wave, or any other medium from which a computer may read at least one of programming code or data. Many of these forms of computer readable media may be involved in carrying one or more sequences of one or more instructions to a processor for execution.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," "includes," "including," or any other variation thereof, are intended to cover a non-exclusive inclusion, such that a process, method, article, or apparatus that comprises or includes a list of elements or steps does not include only those elements or steps but may include other elements or steps not expressly listed or inherent to such process, method, article, or apparatus. An element preceded by "a" or "an" does not, without further constraints, preclude the existence of additional identical elements in the process, method, article, or apparatus that comprises the element. In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventor also contemplates examples in which only those elements shown or described are provided. Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein.

Unless otherwise stated, any and all measurements, values, ratings, positions, magnitudes, sizes, and other specifications that are set forth in this specification, including in the claims that follow, are approximate, not exact. Such amounts are intended to have a reasonable range that is consistent with the functions to which they relate and with what is customary in the art to which they pertain. For example, unless expressly stated otherwise, a parameter value or the like may vary by as much as ±10% from the stated amount.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A wearable device for measuring blood viscosity in a variety of settings or measurement environments, comprising:

an optical sensor configured to sense blood flow rate in a blood vessel of a subject in a setting or environment by providing incident light into the blood vessel of the subject and measuring reflected light, the optical sensor outputting phase shift data representative of the phase shift between the incident light and the reflected light, the optical sensor further comprising at least one carbon nanotube (CNT) that deflects light collected by the optical sensor in accordance with received voltages;

a magnetic field sensor comprising a magnetic field application member that applies a magnetic field to the blood vessel of the subject in the setting or environment and a magnetic field detector that the detects a displacement in the magnetic field indicative of the blood flow rate in the blood vessel of the subject, the magnetic field sensor outputting measured voltages representing the detected displacement;

wherein the at least one CNT of the optical sensor receives the measured voltages from the magnetic field sensor representing the detected displacement and the at least one CNT is deflected by the measured voltages to shift a phase of an output of the optical sensor in accordance with the displacement in the magnetic field;

a processor circuit configured to receive and process the measured voltages from the magnetic field sensor and the phase shift data from the optical sensor to calculate blood viscosity and to generate a medical diagnostic using an indication of the calculated blood viscosity, the processor circuit prioritizing an output of one of the optical sensor or the magnetic field sensor for use in the blood viscosity calculation based on the setting or environment in which the indication of blood viscosity is being calculated; and a display configured to present the medical diagnostic to a user.

2. The wearable device of claim 1, further comprising a fixation member and a device body including at least one of the optical or magnetic field sensors, the fixation member configured to detachably attach the device body to a body part of the subject including the blood vessel.

3. The wearable device of claim 2, wherein at least one of the optical or magnetic field sensors is positioned on an exterior of, or embedded within, the fixation member.

4. The wearable device of claim 2, wherein the at least one of the optical or magnetic field sensors is positioned on an exterior of, or embedded within, the device body.

5. The wearable device of claim 2, wherein the optical and magnetic field sensors are respectively positioned on an exterior of or embedded within the fixation member and on an exterior of or embedded within the device body.

6. The wearable device of claim 2, wherein the optical and magnetic field sensors are respectively disposed on the fixation member and the device body, further comprising magnetic shielding between the magnetic field sensor and the optical sensor, the magnetic shielding adapted to minimize interference between the magnetic field sensor and the optical sensor.

7. The wearable device of claim 1, wherein the processor circuit is configured to determine a composite blood viscosity indication using a combination of two or more viscosity indications respectively determined based on blood parameters sensed respectively by the optical and magnetic field sensors.

8. The wearable device of claim 1, wherein the phase shift of the light by the at least one CNT is indicative of at least one of strain or a shear force in the blood vessel of the subject.

9. The wearable device of claim 1, further comprising an ultrasound sensor configured to sense blood flow rate in the blood vessel of the subject based on a Doppler shift in an ultrasonic wave reflected from the blood vessel of the subject, and the processor circuit is configured to generate the indication of blood viscosity based on the blood flow rate provided by the ultrasound sensor.

10. The wearable device of claim 1, wherein the magnetic field sensor includes:

two or more magnetic field application members configured to apply a magnetic field with respective field orientations or field strengths to the blood vessel of the subject; and a detector configured to measure light absorption when the magnetic field is applied and to determine the displacement in the magnetic field based on the measured light absorption.

11. The wearable device of claim 1, wherein the magnetic field application member is configured to apply a uniform magnetic field of at least 0.1 Tesla to the blood vessel of the subject; and the magnetic field detector is configured to measure the displacement in the magnetic field caused by blood flow in the blood vessel of the subject and to convert the displacement into a measured voltage representing the detected displacement in the magnetic field indicative of the blood flow rate in the blood vessel of the subject.

12. The wearable device of claim 11, wherein the magnetic field detector comprises at least one of a Giant-Magneto-Resistance (GMR) based magnetic sensor or a Tunnel Magneto-Resistance (TMR) effect sensor.

13. The wearable device of claim 1, further comprising a communication circuit configured to communicate with a mobile computing device configured to generate the indication of blood viscosity or the medical diagnostic, or to provide the medical diagnostic to the user.

14. The wearable device of claim 1, wherein the optical sensor is mounted on a first fixation member and the magnetic field sensor is mounted on a second fixation member, the first and second fixation members spaced apart during use to minimize interference between the magnetic field sensor and the optical sensor.

15. The wearable device of claim 14, wherein the first fixation member is adapted for attachment to a wrist adjacent a radial artery of the subject and the second fixation member is adapted for attachment to an upper arm adjacent a brachial artery of the subject, wherein blood flow measurements taken by the optical sensor and the magnetic field sensor are compared by the processor to establish differences in blood flow between the brachial artery and the radial artery.

16. The wearable device of claim 1, further comprising a flexible ultrasound sensor that measures geometry of the blood vessel of the subject and blood pressure and provides the measured geometry of the blood vessel of the subject and blood pressure to the processor circuit for calculation of blood viscosity.

17. The wearable device of claim 1, further comprising at least one dielectric nanoantenna for dissipating heat generated by at least the processor circuit.

18. The wearable device of claim 1, wherein carbon nanotube structures of the at least one CNT form an optical magnetic mirror (OMM) adapted to use the phase shift data to tune a resonance frequency of the OMM.

19. A method for measuring blood viscosity in a variety of settings or measurement environments, comprising:

non-invasively sensing at least one of blood flow rate or blood pressure differential from a subject using an optical sensor configured to sense blood flow rate in a blood vessel of the subject in a setting or environment by providing incident light into the blood vessel of the subject, measuring reflected light, and outputting phase shift data representative of the phase shift between the incident light and the reflected light, the optical sensor comprising at least one carbon nanotube (CNT) that deflects light collected by the optical sensor in accordance with received voltages;

non-invasively sensing at least one of blood flow rate or blood pressure differential from the subject using a magnetic field sensor comprising a magnetic field application member that applies a magnetic field to the blood vessel of the subject in the setting or environment and a magnetic field detector that detects a displacement in the magnetic field indicative of the blood flow rate in the blood vessel of the subject, and outputs measured voltages representing the detected displacement;

providing measured voltages output by the magnetic field sensor representing the detected displacement to the at least one carbon nanotube CNT that is deflected by the measured voltages to shift a phase of an output of the optical sensor in accordance with the displacement in the magnetic field;

providing the measured voltages output by the magnetic field sensor representing the detected displacement and the phase shift data from the optical sensor to at least one processing circuit configured to receive and process the measured voltages from the magnetic field sensor and the phase shift data from the optical sensor to calculate blood viscosity and to generate a medical diagnostic using an indication of the calculated blood viscosity;

prioritizing, by the at least one processing circuit, an output of one of the optical sensor or the magnetic field sensor for use in the blood viscosity calculation based on the setting or environment in which blood viscosity is being calculated;

calculating, by the at least one processing circuit, the blood viscosity using the prioritized output;

generating, by the at least one processing circuit, a medical diagnostic using an indication of the calculated blood viscosity; and presenting, by the at least one processing circuit, the medical diagnostic to a display.

20. The method of claim 19, further comprising detachably attaching a device body including at least one of the optical or magnetic field sensors to a body part of the subject including the blood vessel.

21. The method of claim 20, further comprising applying magnetic shielding between the magnetic field sensor and the optical sensor, the magnetic shielding adapted to minimize interference between the magnetic field sensor and the optical sensor.

22. The method of claim 19, further comprising determining, by the at least one processing circuit, a composite blood viscosity indication using a combination of two or more viscosity indications respectively determined based on blood parameters sensed respectively by the optical and magnetic field sensors.

23. The method of claim 19, further comprising sensing, by an ultrasound sensor, blood flow rate in the blood vessel of the subject based on a Doppler shift in an ultrasonic wave reflected from the blood vessel of the subject, and generating, by the at least one processing circuit, the indication of blood viscosity based on the blood flow rate provided by the ultrasound sensor.

24. The method of claim 19, wherein applying the magnetic field to the blood vessel of the subject comprising applying, by the field application member, a magnetic field with respective field orientations or field strengths to the blood vessel of the subject, further comprising measuring light absorption when the magnetic field is applied and determining the displacement in the magnetic field based on the measured light absorption.

25. The method of claim 19, further comprising applying, by at least one field application member, a uniform magnetic field of at least 0.1 Tesla to the blood vessel of the subject, and measuring, by the magnetic field detector, the displacement in the magnetic field caused by blood flow in the blood vessel of the subject and converting the displacement into a measured voltage representing the detected displacement in the magnetic field indicative of the blood flow rate in the blood vessel of the subject.

26. The method of claim 19, further comprising communicating with a mobile computing device and generating, by the mobile computing device, the indication of blood viscosity or the medical diagnostic or providing the medical diagnostic to the user.

27. The method of claim 19, further comprising mounting the optical sensor on a first fixation member, mounting the magnetic field sensor on a second fixation member, and spacing apart the first and second fixation members during use to minimize interference between the magnetic field sensor and the optical sensor.

28. The method of claim 27, further comprising attaching the first fixation member to a wrist adjacent a radial artery of the subject attaching the second fixation member to an upper arm adjacent a brachial artery of the subject, and comparing blood flow measurements taken by the optical sensor and the magnetic field sensor to establish differences in blood flow between the brachial artery and the radial artery.

29. The method of claim 19, wherein carbon nanotube structures of the at least one CNT form an optical magnetic mirror (OMM) further comprising using the phase shift data to tune a resonance frequency of the OMM.

30. A non-transitory computer-readable storage medium that stores instructions that when executed by at least one processor cause the at least one processor to perform a method for measuring blood parameters, including:

non-invasively sensing at least one of blood flow rate or blood pressure differential from a subject using an optical sensor configured to sense blood flow rate in a blood vessel of the subject in a setting or environment by providing incident light into the blood vessel of the subject, measuring reflected light, and outputting phase shift data representative of the phase shift between the incident light and the reflected light, the optical sensor comprising at least one carbon nanotube (CNT) that deflects light collected by the optical sensor in accordance with received voltages;

non-invasively sensing at least one of blood flow rate or blood pressure differential from the subject using a magnetic field sensor comprising a magnetic field application member that applies a magnetic field to the blood vessel of the subject in the setting or environment and a magnetic field detector that detects a displacement in the magnetic field indicative of the blood flow rate in the blood vessel of the subject and outputs measured voltages representing the detected displacement;

providing measured voltages output by the magnetic field sensor representing the detected displacement to the at least one carbon nanotube CNT that is deflected by the measured voltages to shift a phase of an output of the optical sensor in accordance with the displacement in the magnetic field;

receiving the measured voltages output by the magnetic field sensor representing the detected displacement and the phase shift data from the optical sensor;

processing the measured voltages from the magnetic field sensor and the phase shift data from the optical sensor to calculate blood viscosity and to generate a medical diagnostic using an indication of the calculated blood viscosity by performing the steps of:

prioritizing an output of one of the optical sensor or the magnetic field sensor for use in the blood viscosity calculation based on the setting or environment in which blood viscosity is being calculated, calculating the blood viscosity using the prioritized output, and generating a medical diagnostic using an indication of the calculated blood viscosity; and presenting the medical diagnostic to a display.

\* \* \* \* \*